(12) United States Patent
Amasaki et al.

(10) Patent No.: US 8,975,314 B2
(45) Date of Patent: Mar. 10, 2015

(54) TRIAZINE DERIVATIVE AND ULTRAVIOLET ABSORBER

(71) Applicant: FUJIFILM Corporation, Tokyo (JP)

(72) Inventors: Ichiro Amasaki, Fujinomiya (JP); Keizo Kimura, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/229,187

(22) Filed: Mar. 28, 2014

(65) Prior Publication Data

US 2014/0213703 A1 Jul. 31, 2014

Related U.S. Application Data

(63) Continuation of application No. PCT/JP2012/074347, filed on Sep. 24, 2012.

(30) Foreign Application Priority Data

Sep. 29, 2011 (JP) ................. 2011-215631

(51) Int. Cl.
*C07D 251/24* (2006.01)
*C08K 5/3492* (2006.01)
*C07D 409/14* (2006.01)

(52) U.S. Cl.
CPC .......... *C08K 5/34926* (2013.01); *C07D 409/14* (2013.01); *C07D 251/24* (2013.01); *C08K 5/3492* (2013.01)
USPC .......................................... 524/100; 544/216

(58) Field of Classification Search
CPC .............................. C07D 251/24; C08K 5/3492
USPC .............................................. 524/100; 544/216
See application file for complete search history.

(56) References Cited

U.S. PATENT DOCUMENTS

| | | |
|---|---|---|
| 5,476,937 A | 12/1995 | Stevenson et al. |
| 5,681,955 A | 10/1997 | Stevenson |
| 5,760,227 A | 6/1998 | Mura |
| 2010/0174015 A1* | 7/2010 | Negishi et al. ............... 524/100 |

FOREIGN PATENT DOCUMENTS

| | | |
|---|---|---|
| JP | 8-20579 A | 1/1996 |
| JP | 8-53427 A | 2/1996 |
| JP | 2006-225320 A | 8/2006 |
| JP | 2006-225322 A | 8/2006 |
| JP | 3965631 B2 | 8/2007 |

OTHER PUBLICATIONS

STN Structure Search (Dec. 30, 2014).*
International Search Report issued in PCT/JP2012/074347, mailed on Dec. 25, 2012.
PCT/ISA/237—Issued in PCT/JP2012/074347, mailed on Dec. 25, 2012.

* cited by examiner

*Primary Examiner* — Vu A Nguyen
(74) *Attorney, Agent, or Firm* — Birch, Stewart, Kolasch & Birch, LLP

(57) ABSTRACT

There is provided a new triazine-based compound which is useful as an ultraviolet absorber having excellent light resistance, heat resistance and ultraviolet ray shielding effect. A compound represented by the following general formula (1),

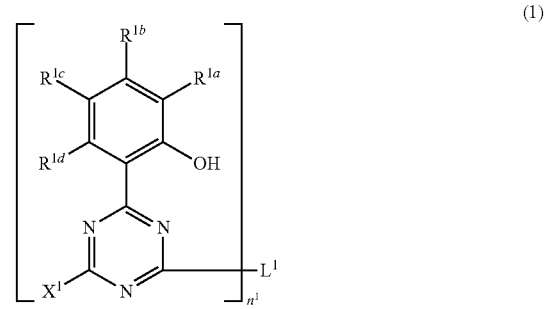

(1)

in the general formula (1), $L^1$ represents a divalent to decavalent aromatic ring residue or a divalent to decavalent heterocycle residue, $n^1$ represents an integer of 2 to 10, $X^1$ represents a hydrogen atom or a substituent, $R^{1a}$, $R^{1b}$, $R^{1c}$ and $R^{1d}$ each independently represent a hydrogen atom or a substituent and may be bonded to each other to form a ring.

13 Claims, No Drawings

TRIAZINE DERIVATIVE AND ULTRAVIOLET ABSORBER

CROSS REFERENCE TO RELATED APPLICATIONS

This application is a continuation of PCT International Application No. PCT/JP2012/074347 filed on Sep. 24, 2012, which claims priority under 35 U.S.C. 119(a) to Application No. 2011-215631 filed on Sep. 29, 2011 in Japan, all of which are hereby expressly incorporated by reference into the present application.

BACKGROUND OF THE INVENTION

1. Field of the Invention

The present invention relates to a new triazine derivative and an ultraviolet absorber.

2. Description of the Related Art

Imparting an ultraviolet ray absorptivity has been performed by using an ultraviolet absorber together with various resins or the like in the relate art. There are cases when an inorganic-based ultraviolet absorber and an organic-based ultraviolet absorber are used as an ultraviolet absorber. Although an inorganic-based ultraviolet absorber is superior in durability such as weather resistance or heat resistance, a degree of freedom in selection is low since an absorption wavelength is determined depending on a band gap of a compound. Therefore, the coloration occurs since there is not an inorganic-based ultraviolet absorber which can absorb up to a long-wavelength ultraviolet ray (UV-A) with wavelength in the vicinity of 400 nm and an inorganic-based ultraviolet absorber which absorbs a long-wavelength ultraviolet ray also absorbs visible rays.

In contrast, since an organic-based ultraviolet absorber has a high degree of freedom in structural design of an absorber, it is possible to obtain one having various absorption wavelengths by contriving the structure of an absorber.

Materials which are applied to a solar cell or the like for which the development has been proceeded in recent years are required to be exposed to solar light outdoors for a long time, and it was inevitable that the quality deteriorated by exposure of an ultraviolet ray over a long time. For this reason, an organic-based ultraviolet absorber compound which exhibits a shielding effect in up to an UV-A region and has excellent light resistance in addition to durability such as heat resistance has been required.

In the related art, systems in which various organic-based ultraviolet absorbers are used have been studied, and a triazole-base and a triazine-based ultraviolet absorber are disclosed. Trisaryl-s-triazine having an alkoxy group and a hydroxy group at a specific position is described in JP3965631B. A compound in which trisaryl-s-triazine having a hydroxy group is multimerized through a linking group is described in JP 1996-53427A (JP-H08-53427A).

Furthermore, as a well-known triazine-based compound, a compound in which diphenyl-triazine which is expected as an organic material for organic electroluminescence element or the like is dimerized through a linking group is described in JP2006-225322A, JP2006-225320A and JP1996-20579A (JP-H08-20579A).

SUMMARY OF THE INVENTION

As a result of studies of the present inventors, it was found that compounds in which a maximum absorption wavelength is in a long wavelength ultraviolet ray region are inferior in light resistance and decrease an ultraviolet ray shielding effect over time, besides heat resistance is not sufficient as to a compound described in JP3965631B. It was found that light resistance is insufficient since the conjugation of a compound in a part of a linking group is blocked as to a compound described in JP1996-53427A (JP-H08-53427A). In addition, as to a compound described in JP2006-225322A and JP2006-225320A, there was no description of an ultraviolet absorbing ability and there was room for studying as an organic material for ultraviolet absorber.

The present invention has been made in view of the above problem, an object thereof is to provide a new triazine-based compound which is useful as an ultraviolet absorber which exhibits a high ultraviolet ray shielding effect and has excellent light resistance and heat resistance.

As a result of studies in detail as to a triazine-based compound, the present inventors found a compound having a structure which is not known in the related art. In addition, it was found that the compound described above is useful as an ultraviolet absorber having excellent light resistance, heat resistance and ultraviolet ray shielding effect as never before, and the completion of the present invention has been reached.

An object of the present invention is achieved by a compound described below, an ultraviolet absorber containing the compound and a resin composition containing at least the compound and a resin.

A compound of the present invention is represented by the following general formula (1).

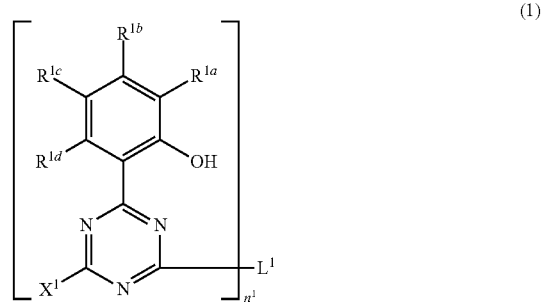

In the general formula (1), $L^1$ represents a divalent to decavalent aromatic ring residue or a divalent to decavalent heterocycle residue $n^1$ represents an integer of 2 to 10. $X^1$ represents a hydrogen atom or a substituent. $R^{1a}$, $R^{1b}$, $R^{1c}$ and $R^{1d}$ each independently represent a hydrogen atom or a substituent and may be bonded to each other to form a ring.

Preferably, $X^1$ in the general formula (1) represents an aromatic ring residue or a heterocycle residue.

In addition, preferably, the compound represented by the general formula (1) is a compound represented by the following general formula (2).

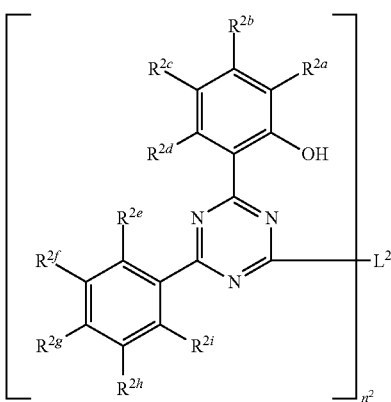

(2)

In the general formula (2), $L^2$ represents a divalent to decavalent aromatic ring residue or a divalent to decavalent heterocycle residue. $n^2$ represents an integer of 2 to 10. $R^{2a}$, $R^{2b}$, $R^{2c}$ and $R^{2d}$ each independently represent a hydrogen atom or a substituent and may be bonded to each other to form a ring. In addition, $R^{2e}$, $R^{2f}$, $R^{2g}$, $R^{2h}$ and $R^{2i}$ each independently represent a hydrogen atom or a substituent and may be bonded to each other to form a ring.

In addition, preferably, any of $R^{2e}$, $R^{2f}$, $R^{2g}$, $R^{2h}$ and $R^{2i}$ in the general formula (2) represents an electron-withdrawing group. In addition, in a case where $R^{2e}$, $R^{2f}$, $R^{2g}$, $R^{2h}$ and $R^{2i}$ are bonded to each other to form a ring, the ring has an electron-withdrawing group as a substituent. In addition, preferably, the electron-withdrawing group is represented by —CN or —COOR$^r$. Here, R$^r$ represents a hydrogen atom or a substituent.

In addition, preferably, $L^1$ in the general formula (1) or $L^2$ in the general formula (2) is a group represented by a divalent aromatic ring residue or heterocycle residue. In addition, preferably, $L^1$ in the general formula (1) or $L^2$ in the general formula (2) is a divalent aromatic ring residue and the aromatic ring residue is a benzene ring or a naphthalene ring.

In addition, preferably, the compound represented by the general formula (1) or the general formula (2) is a compound represented by the following general formula (3).

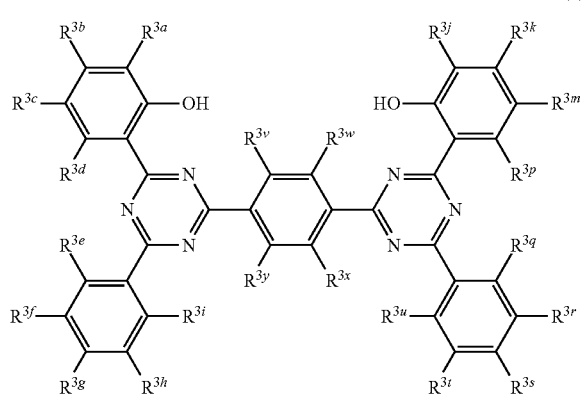

(3)

In the general formula (3), $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3m}$, $R^{3p}$, $R^{3q}$, $R^{3r}$, $R^{3s}$, $R^{3t}$, $R^{3u}$, $R^{3v}$, $R^{3w}$, $R^{3x}$ and $R^{3y}$ each independently represent a hydrogen atom or a substituent and may be bonded to each other to form a ring.

An ultraviolet absorber of the present invention contains the compound of the present invention.

A resin composition of the present invention contains at least the compound of the present invention and a resin.

A compound of the present invention has excellent light resistance, heat resistance and ultraviolet ray shielding effect as never before and can be suitably used as an ultraviolet absorber.

DESCRIPTION OF THE PREFERRED EMBODIMENTS

Hereinafter, description will be given of the present invention in detail.

[Compound Represented by General Formula (1)]

The present invention relates to a compound (a triazine derivative) represented by the following general formula (1). Since the compound represented by the general formula (1) has a hydroxyl group in a structure thereof, the compound is thermally inactivated by the migration of protons in a light excitation state and thus light resistance is excellent. In addition, since the compound is multimerized through a linking group, the compound becomes to have a high molecular weight and the compound is hardly volatilized, and thus heat resistance is excellent. Furthermore, since a conjugated system is retained in the entire area of a structure of the compound, the compound has a characteristic which is excellent in light resistance by effectively converting light energy into thermal energy.

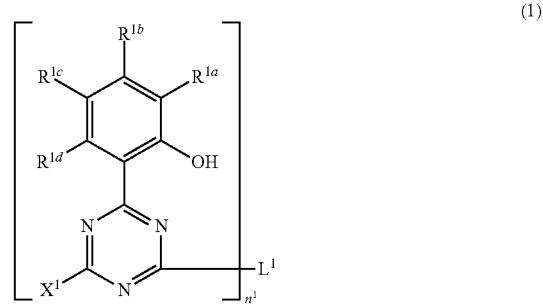

(1)

In the general formula (1), $L^1$ represents a divalent to decavalent aromatic ring residue or a divalent to decavalent heterocycle residue $n^1$ represents an integer of 2 to 10. $X^1$ represents a hydrogen atom or a substituent. $R^{1a}$, $R^{1b}$, $R^{1c}$ and $R^{1d}$ each independently represent a hydrogen atom or a substituent and may be bonded to each other to form a ring.

$L^1$ in the general formula (1) represents a divalent to decavalent aromatic ring residue or heterocycle residue.

$L^1$ may be a polycyclic structure having an aromatic ring and heterocycle structure described below and may be a structure in which a plurality of rings described below are linked by a single bond.

As a divalent to decavalent aromatic ring residue represented by $L^1$ in the general formula (1), a group in which one hydrogen atom is removed from a benzene ring, a naphthalene ring, an anthracene ring, a naphthacene ring, a pentacene ring, a benzopyrene ring, a chrysene ring, a pyrene ring, a triphenylene ring, a corannulene ring, a coronene ring, an ovalene ring or a phenanthrene ring, or a group in which a plurality of these rings are linked is included. In addition, these rings may have a substituent.

In the present invention, as an aromatic ring, a group in which one hydrogen atom is removed from a benzene ring, a naphthalene ring or a biphenyl ring is preferable, and a group in which one hydrogen atom is removed from a benzene ring or a naphthalene ring is more preferable from the viewpoint of an ultraviolet ray shielding effect and light resistance.

As a divalent to decavalent heterocycle residue represented by $L^1$ in the general formula (1), a group in which one hydrogen atom is removed from a pyrrole ring, a pyrazole ring, an imidazole ring, a 1,2,3-triazole ring, a 1,2,4-triazole ring, a pyridine ring, a pyridazine ring, a pyrimidine ring, a pyrazine ring, a 1,3,5-triazine ring, a furan ring, a thiophene ring, an oxazole ring, an isoxazole ring, a thiazole ring, an isothiazole ring, a 1,2,3-oxadiazole ring or a 1,3,4-thiadiazole ring is included. In addition, these rings may have a substituent. A group in which one hydrogen atom is removed from a pyrrole ring, a pyridine ring, a furan ring or a thiophene ring is preferable. A group in which one hydrogen atom is removed from a pyridine ring or a thiophene ring is more preferable. A group in which one hydrogen atom is removed from a thiophene ring is further preferable.

As a substituent in a case where an aromatic ring or heterocycle represented by $L^1$ has a substituent (hereinafter, referred to as a substituent R), for example, a halogen atom (for example, a fluorine atom, a chlorine atom, a bromine atom and an iodine atom), an alkyl group having 1 to 20 carbon atoms (for example, methyl and ethyl), an aryl group having 6 to 20 carbon atoms (for example, phenyl and naphthyl), a cyano group, a carboxyl group, an alkoxycarbonyl group (for example, methoxycarbonyl), an aryloxycarbonyl group (for example, phenoxycarbonyl), a carbamoyl group (for example, carbamoyl, N-phenylcarbamoyl and N,N-dimethylcarbamoyl), an alkyl carbonyl group (for example, acetyl), an aryl carbonyl group (for example, benzoyl), a nitro group, an amino group (for example, amino, dimethylamino and anilino), an acylamino group (for example, acetamide and ethoxy carbonyl amino), a sulfonamide group (for example, methanesulfonamide), an imide group (for example, succinimide and phthalimide), an imino group (for example, benzylidene amino), a hydroxy group, an alkoxy group having 1 to 20 carbon atoms (for example, methoxy), an aryloxy group (for example, phenoxy), an acyloxy group (for example, acetoxy), an alkylsulfonyloxy group (for example, methanesulfonyloxy), an arylsulfonyloxy group (for example, benzenesulfonyloxy), a sulfo group, a sulfamoyl group (for example, sulfamoyl and N-phenylsulfamoyl), an alkylthio group (for example, methylthio), an arylthio group (for example, phenylthio), an alkylsulfonyl group (for example, methanesulfonyl), an arylsulfonyl group (for example, benzenesulfonyl), a heterocycle group having 6 to 20 carbon atoms (for example, pyridyl and morpholino), and the like are included.

In addition, the substituent R may be further substituted and in a case where there are a plurality of substituents, they may be the same as or different from each other. In this case, as an example of the substituent, the substituent R described above can be included. In addition, the substituents may be bonded to each other to form a ring.

A substituent in a case where an aromatic ring residue or heterocycle residue represented by $L^1$ has a substituent is preferably an alkyl group having 1 to 20 carbon atoms and more preferably an alky group having 1 to 6 carbon atoms.

$L^1$ is preferably a divalent to tetravalent aromatic ring residue or heterocycle residue, more preferably a divalent or a trivalent aromatic ring residue or heterocycle residue, further preferably a divalent aromatic ring residue, particularly preferably a divalent benzene ring or naphthalene ring residue from the viewpoint of an ultraviolet ray shielding effect and light resistance, and most preferably a divalent benzene ring residue from the viewpoint of light resistance.

In addition, in a case where $L^1$ represents a divalent benzene ring residue, $L^1$ represents 1,2-phenylene, 1,3-phenylene or 1,4-phenylene, 1,3-phenylene or 1,4-phenylene is preferably from the viewpoint of an ultraviolet ray shielding effect, and 1,4-phenylene is more preferably from the viewpoint of an ultraviolet ray shielding effect.

$n^1$ in the general formula (1) described above represents an integer of 2 to 10.

$n^1$ is preferably an integer of 2 to 5, more preferably 2 or 3, and further preferably 2. This is because an ultraviolet ray shielding effect and light resistance are excellent.

$X^1$ in the general formula (1) described above represents a hydrogen atom or a substituent.

As a substituent represented by $X^1$, the substituent R described above is included, an alkyl group, an alkoxycarbonyl group, an aryl group having 6 to 20 carbon atoms or a heterocycle group having 6 to 20 carbon atoms is preferable, an aryl group having 6 to 20 carbon atoms or a heterocycle group having 6 to 20 carbon atoms having high ultraviolet absorbing effect is more preferable, and a benzene ring, a naphthalene ring, a thiophene ring and a biphenyl ring are more preferable.

A substituent represented by $X^1$ may be further substituted, and it is preferred to substituted with an electron-withdrawing group.

In the present invention, $X^1$ is preferably an aryl group having 6 to 20 carbon atoms or a heterocycle group having 6 to 20 carbon atoms which is unsubstituted or is substituted with an electron-withdrawing group, and a benzene ring, a naphthalene ring, a thiophene ring and a biphenyl ring which are unsubstituted or are substituted with an electron-withdrawing group are more preferable.

In a case where $X^1$ represents a benzene ring which is substituted with an electron-withdrawing group, a phenyl group which is substituted with an electron-withdrawing group at o-position or p-position is preferable, and a phenyl group which is substituted with an electron-withdrawing group at p-position is more preferable. This is because light resistance is excellent.

In a case where $X^1$ represents a naphthalene ring which is substituted with an electron-withdrawing group, a 2-naphthyl group which is substituted with an electron-withdrawing group at 3-position or 6-position is preferable, and a 2-naphthyl group which is substituted with an electron-withdrawing group at 6-position is more preferable. This is because an ultraviolet ray shielding effect is excellent.

As an electron-withdrawing group described above, $COOR^r$ ($R^r$ represents a hydrogen atom or a monovalent substituent, a hydrogen atom and an alkyl group are included, and an alkyl group is preferable.), $CONR^s_2$ ($R^s$ represents a hydrogen atom or a monovalent substituent, for example, a hydrogen atom, an alkyl group having 1 to 20 carbon atoms, an aryl group having 6 to 20 carbon atoms and a heterocycle group having 6 to 20 carbon atoms are included, and a hydrogen atom is preferable.), a cyano group, a nitro group, $SO_3M$ (M represents a hydrogen atom or an alkali metal), an acyl group, a formyl group, an acyloxy group, an acylthio group, an alkyloxy carbonyl group, an aryloxycarbonyl group, a dialkyl phosphono group, a diarylphosphono group, a dialkylphosphinyl group, a diarylphosphinyl group, a phosphoryl group, an alkylsulfinyl group, an arylsulfinyl group, an alkylsulfonyl group, an arylsulfonyl group, a sulfamoyl group, a thiocyanate group, a thiocarbonyl group, an imino group, an imino group which is substituted with an N atom, a carboxy group (or a salt thereof), an alkyl group which is substituted with at least two halogen atoms or more (for example, $CF_3$), an alkoxy group which is substituted with at least two halogen atoms or more, an aryloxy group which is substituted with at least two halogen atoms or more, an acylamino group, an alkylamino group which is substituted with at least two halogen atoms or more, an alkylthio group which is substituted with at least two halogen atoms or more, an aryl group which is substituted with other electron-withdrawing group, a heterocycle group, an azo group, a selenocyanate group, and the like are included.

—COOR$^r$ or a cyano group is preferable from the viewpoint of light resistance.

$R^{1a}$, $R^{1b}$, $R^{1c}$ and $R^{1d}$ in the general formula (1) described above each independently represent a hydrogen atom or a substituent and may be bonded to each other to form a ring. $R^{1a}$ and $R^{1b}$, $R^{1b}$ and $R^{1c}$, or $R^{1c}$ and $R^{1d}$ are preferably bonded to each other to form a ring, and as a ring which is formed, a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, a phosphole ring, and the like are included. In addition, these rings may further have a substituent.

As a substituent represented by $R^{1a}$, $R^{1b}$, $R^{1c}$ and $R^{1d}$ described above, a hydrogen atom, a substituted or unsubstituted alkyl group having 1 to 20 carbon atoms, a cyano group, a carboxyl group, a substituted or unsubstituted alkoxycarbonyl group, a substituted or unsubstituted carbamoyl group, a substituted or unsubstituted alkycarbonyl group, a nitro group, a substituted or unsubstituted amino group, a hydroxy group, an alkoxy group having 1 to 20 carbon atoms, a substituted or unsubstituted aryloxy group, a substituted or unsubstituted sulfamoyl group, a thiocyanate group or a substituted or unsubstituted alkyl sulfonyl group is included, and a substituent in a case of having a substituent includes a hydrogen atom, an alkyl group having 1 to 20 carbon atoms, a cyano group, a carboxyl group, an alkoxycarbonyl group, a carbamoyl group, a alkycarbonyl group, a nitro group, an amino group, a hydroxy group, an alkoxy group having 1 to 20 carbon atoms, an aryloxy group, a sulfamoyl group, a thiocyanate group or an alkylsulfonyl group.

In the present invention, $R^{1a}$, $R^{1b}$, $R^{1c}$ and $R^{1d}$ described above are preferably a hydrogen atom from the viewpoint of light resistance, and $R^{1a}$, $R^{1b}$, $R^{1c}$ and $R^{1d}$ further preferably represent a hydrogen atom.

The compound represented by the general formula (1) described above in the present invention is preferably a compound represented by the following general formula (2) from the viewpoint of light resistance.

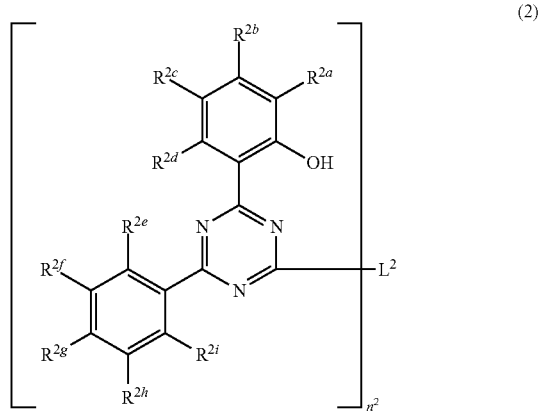

(2)

In the general formula (2), $L^2$ represents a divalent to decavalent aromatic ring residue or a divalent to decavalent heterocycle residue. $n^2$ represents an integer of 2 to 10. $R^{2a}$, $R^{2b}$, $R^{2c}$ and $R^{2d}$ each independently represent a hydrogen atom or a substituent and may be bonded to each other to form a ring. In addition, $R^{2e}$, $R^{2f}$, $R^{2g}$, $R^{2h}$ and $R^{2i}$ each independently represent a hydrogen atom or a substituent and may be bonded to each other to form a ring.

In the general formula (2), $L^2$, $n^2$, $R^{2a}$, $R^{2b}$, $R^{2c}$ and $R^{2d}$ have the same meanings as $L^1$, $n^1$, $R^{1a}$, $R^{1b}$, $R^{1c}$ and $R^{1d}$ in the general formula (1) described above and the preferred ranges are also the same.

In the general formula (2), $R^{2e}$, $R^{2f}$, $R^{2g}$, $R^{2h}$ and $R^{2i}$ each independently represent a hydrogen atom or a substituent and may be bonded to each other to form a ring.

The substituents represented by $R^{2e}$, $R^{2f}$, $R^{2g}$, $R^{2h}$ and $R^{2i}$ in the general formula (2) described above have the same meanings as the substituent in a case where a substituent represented by $X^1$ in the general formula (1) described above is further substituted and the preferred ranges are also the same.

In a case where $R^{2c}$, $R^{2f}$, $R^{2h}$, and $R^{2i}$ are bonded to each other to form a ring, $R^{2c}$ and $R^{2f}$, $R^{2f}$ and $R^{2g}$, $R^{2g}$ and $R^{2h}$, or $R^{2h}$ and $R^{2i}$ are preferably bonded to each other to form a ring, and as a ring which is formed, a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring or a phosphole ring is included. In addition, these rings may further have a substituent.

In a case where $R^{2c}$, $R^{2f}$, $R^{2g}$, $R^{2h}$ and $R^{2i}$ are bonded to each other to form a ring, it is preferred to form a benzene ring.

This is because an ultraviolet ray shielding effect becomes higher, due to the absorption peculiar to naphthalene ring in a case where $R^{2e}$, $R^{2f}$, $R^{2g}$, $R^{2h}$ and $R^{2i}$ are bonded to each other to form a benzene ring and a naphthalene ring is formed as a whole.

In the present invention, any of $R^{2e}$, $R^{2f}$, $R^{2g}$, $R^{2h}$ and $R^{2i}$ in the general formula (2) described above represents an electron-withdrawing group. Alternatively, in a case where $R^{2c}$, $R^{2f}$, $R^{2g}$, $R^{2h}$ and $R^{2i}$ are bonded to each other to form a ring, the ring preferably has an electron-withdrawing group as a substituent, from the viewpoint of light resistance, and the electron-withdrawing group described above is particularly preferably —CN or —COOR$^r$.

This is because excellent light resistance is exhibited since an excited lifetime becomes shorter due to LUMO being stabilized by having an electron-withdrawing group in the compound.

As an embodiment in the general formula (2), $R^{2e}$, $R^{2f}$, $R^{2g}$, $R^{2h}$ and $R^{2i}$ is preferably a hydrogen atom. In addition, as another embodiment, it is preferred that $R^{2e}$ be an electron-withdrawing group and $R^{2f}$, $R^{2g}$, $R^{2h}$ and $R^{2i}$ be a hydrogen atom, $R^{2g}$ be an electron-withdrawing group and $R^{2e}$, $R^{2f}$, $R^{2h}$ and $R^{2i}$ be a hydrogen atom, or $R^{2i}$ be an electron-withdrawing group and $R^{2e}$, $R^{2f}$, $R^{2g}$ and $R^{2h}$ be a hydrogen atom.

The compound represented by the general formula (1) described above or the general formula (2) described above in the present invention is more preferably a compound represented by the following general formula (3), from the viewpoint of an ultraviolet ray shielding effect. This is because there is no possibility that the conjugation is blocked by setting a linking group for forming a multimer to a benzene ring and an ultraviolet ray absorption effectively increases due to the stretching vibration by setting a linking position thereof to p-position.

(3)

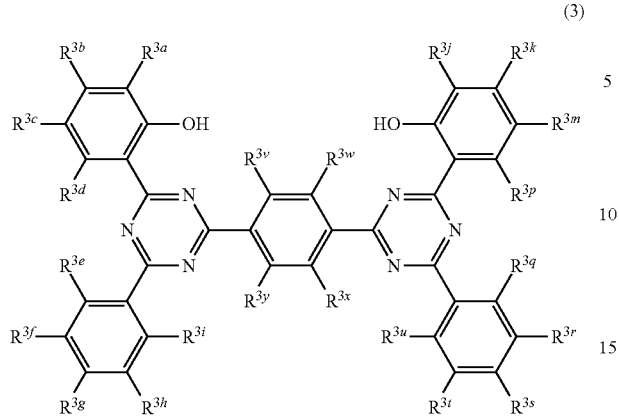

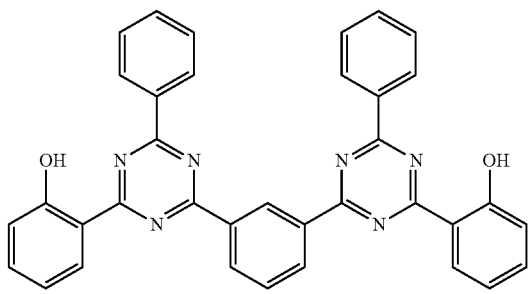

2

In the general formula (3), $R^{3a}, R^{3b}, R^{3c}, R^{3d}, R^{3e}, R^{3f}, R^{3g}, R^{3h}, R^{3i}, R^{3j}, R^{3k}, R^{3m}, R^{3p}, R^{3q}, R^{3r}, R^{3s}, R^{3t}, R^{3u}, R^{3v}, R^{3x}$ and $R^{3y}$ each independently represent a hydrogen atom or a substituent and may be bonded to each other to form a ring.

In the general formula (3), $R^{3a}, R^{3b}, R^{3c}, R^{3d}, R^{3j}, R^{3k}, R^{3m}$ and $R^{3p}$ have the same meanings as $R^{1a}, R^{1b}, R^{1c}$ and $R^{1d}$ in the general formula (1) described above and the preferred ranges are also the same.

In addition, in the general formula (3), $R^{3e}, R^{3f}, R^{3g}, R^{3h}, R^{3i}, R^{3q}, R^{3r}, R^{3s}, R^{3t}$ and $R^{3u}$ have the same meanings as $R^{2e}, R^{2f}, R^{2g}, R^{2h}$ and $R^{2i}$ in the general formula (2) described above and the preferred ranges are also the same.

In the general formula (3), $R^{3v}, R^{3w}, R^{3x}$ and $R^{3y}$ each independently represent a hydrogen atom or a substituent. A substituent has the same meanings as a substituent in a case where a divalent to decavalent aromatic ring residue or a divalent to decavalent heterocycle residue represented by $L^1$ in the general formula (1) described above has a substituent and the preferred ranges are also the same.

In the present invention, $R^{3v}, R^{3w}, R^{3x}$ and $R^{3y}$ described above are preferably a hydrogen atom or an alkoxyl group having 1 to 20 carbon atoms from the viewpoint of an ultraviolet ray shielding effect, and $R^{3v}, R^{3w}, R^{3x}$ and $R^{3y}$ more preferably represent a hydrogen atom.

Specific examples of the compounds represented by the general formulae (1) to (3) described above are shown below, however, the present invention is not limited thereto.

Moreover, Me in the following specific examples represents a methyl group.

1

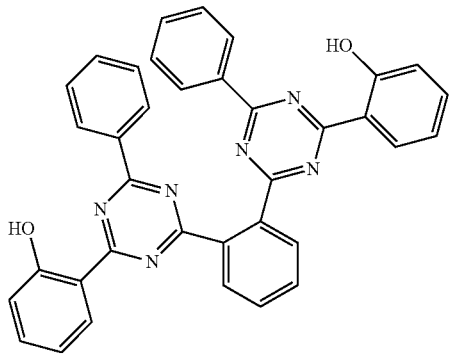

3

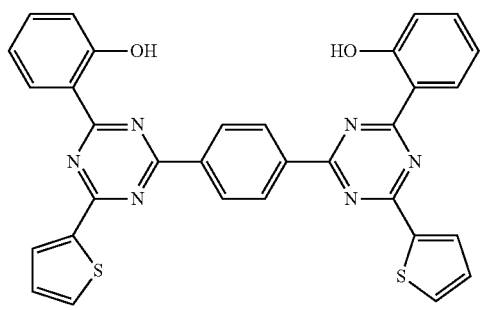

4

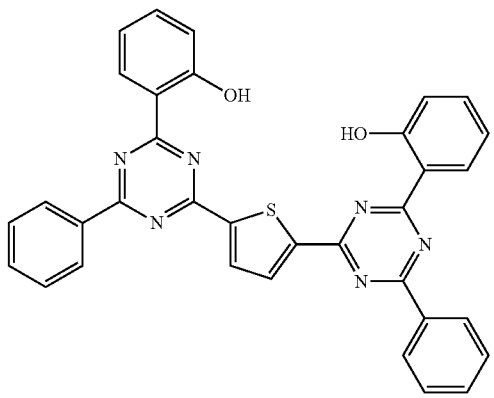

5

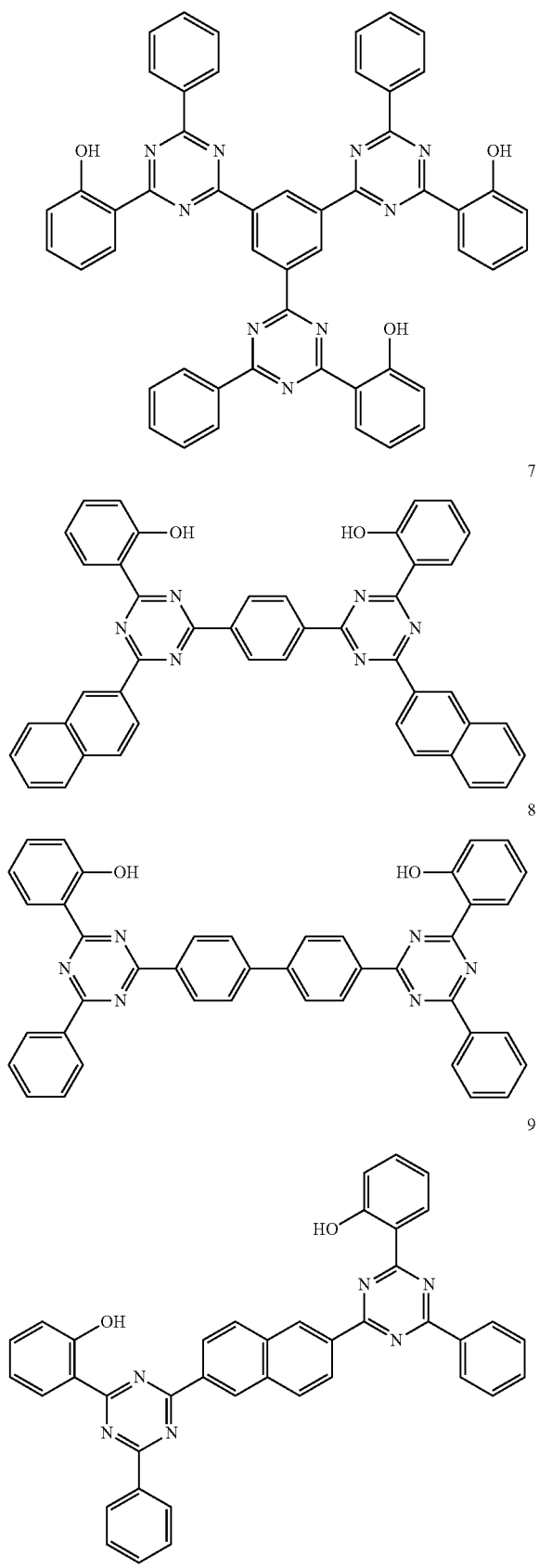
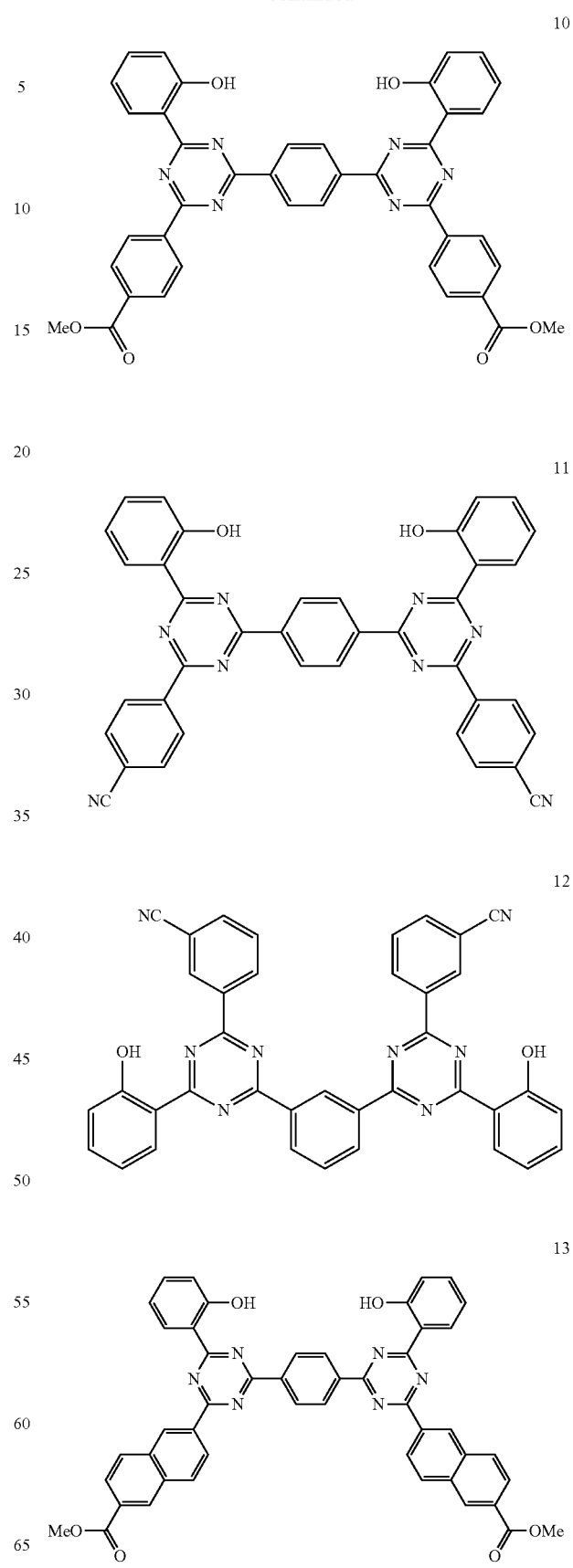

14
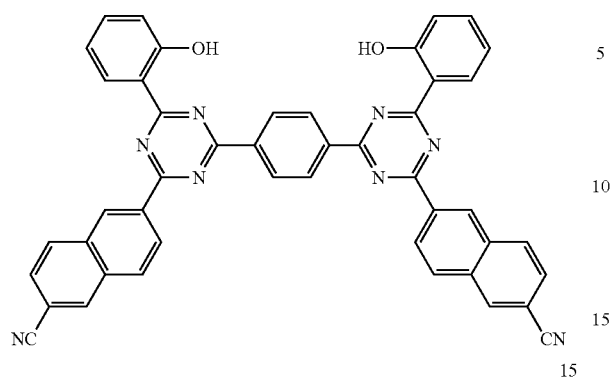
15
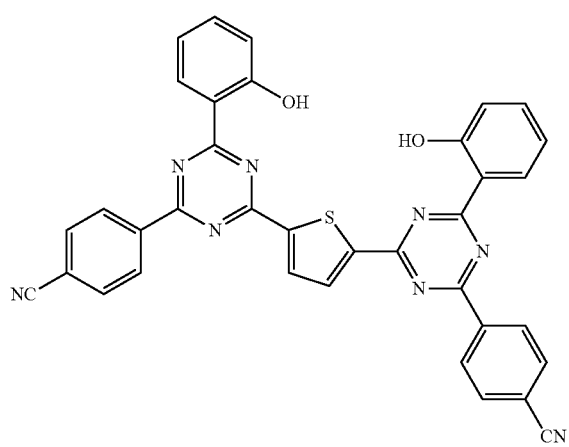
16
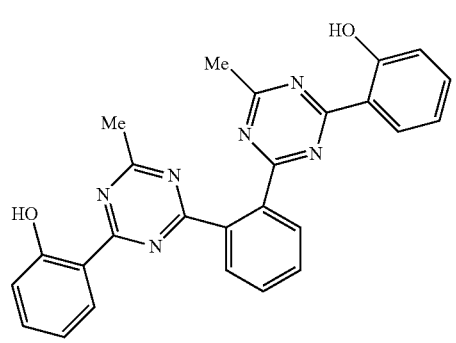
17
18
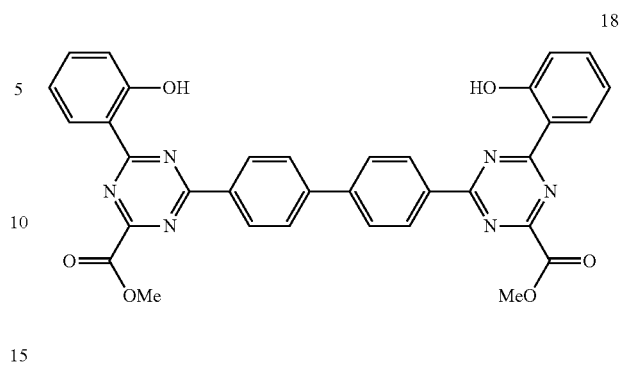
19
20
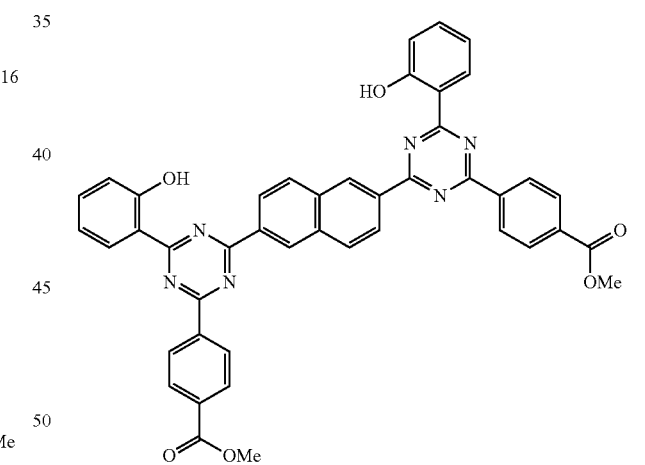
21
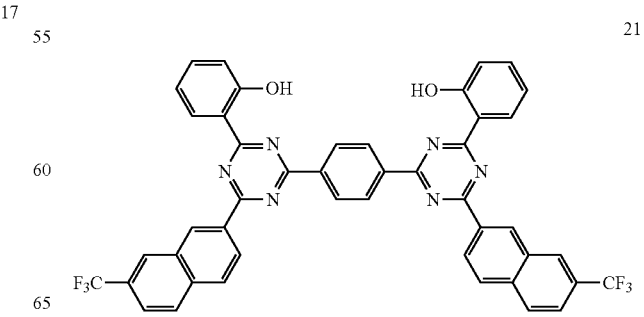

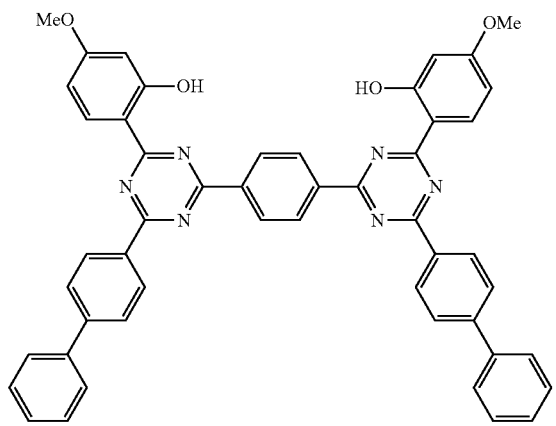
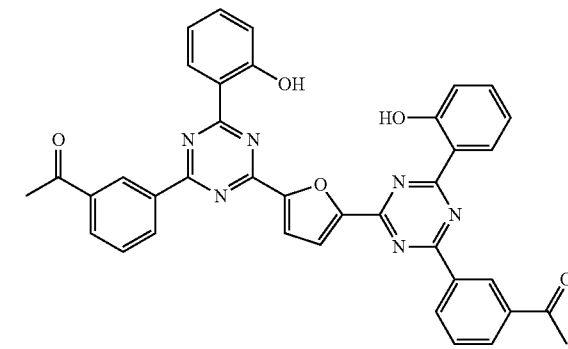
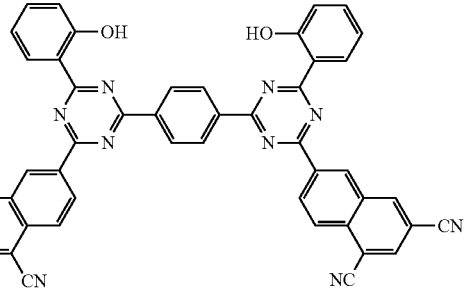
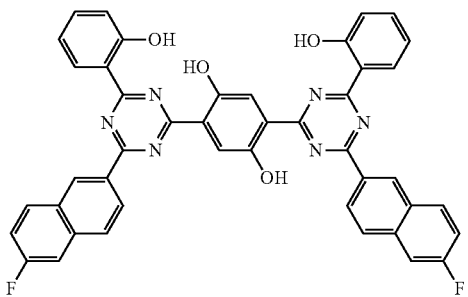
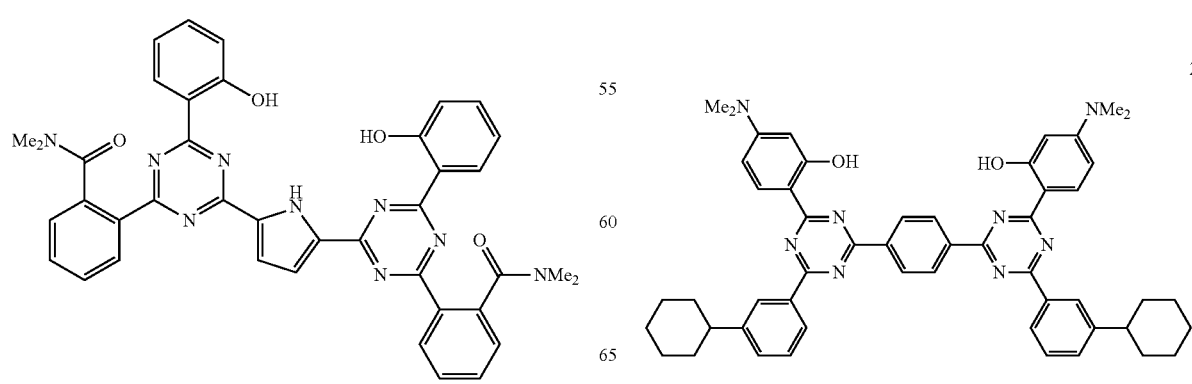

-continued

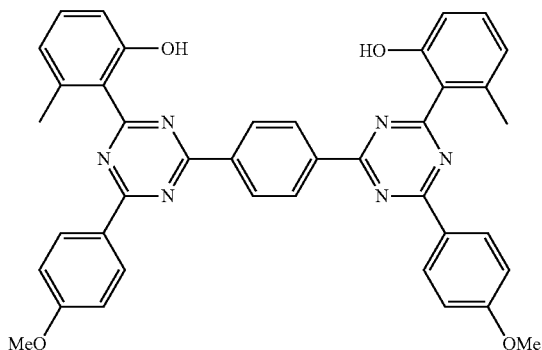

30

The compounds represented by the general formulae (1) to (3) described above are capable of taking a tautomer depending on structures and environments placed thereof. In the present invention, one of typical forms is described; however, a tautomer which is different from that described in the present invention is also included in the compound of the present invention.

The compounds represented by the general formulae (1) to (3) described above may contain an isotope (for example, $^2$H, $^3$H, $^{13}$C, $^{15}$N, $^{17}$O, $^{18}$O, or the like).

The compounds represented by the general formulae (1) to (3) described above can be synthesized by an arbitrary method.

For example, it is possible to synthesize with reference to well-known Patent Documents or Non-Patent Documents, for example, JP1995-188190A (JP-H07-188190A), JP1999-315072A (JP-H11-315072A), 1P2001-220385A, "Dyestuffs & Chemicals" Vol. 40, No. 12 (1995), pp. 325 to 339, and the like. Specifically, it is possible to synthesize by the Friedel-Crafts reaction using cyanuric chloride with an aromatic ring, a heterocycle an alkyl halide, or the like. In addition, it is also possible to synthesize by a reaction of benzoxazinone with amidine, or the like.

The compound of the present invention is particularly suitable for stabilizing an organic material with respect to damages due to light, oxygen or heat. Above all, the compounds represented by the general formulae (1) to (3) described above in the present invention can be suitably used as a light stabilizer, especially, as an ultraviolet absorber.

[Ultraviolet Absorber]

The compounds represented by the general formulae (1) to (3) in the present invention are useful as an ultraviolet absorber.

Hereinafter, description will be given of the ultraviolet absorbers represented by the general formulae (1) to (3) described above.

The preferred examples and the specific examples of the ultraviolet absorbers represented by the general formulae (1) to (3) in the present invention can include the same as the preferred examples and the specific examples of the compounds represented by the general formulae (1) to (3) in the present invention.

The ultraviolet absorbers of the present invention are represented by the general formulae (1) to (3). Since the ultraviolet absorbers represented by the general formulae (1) to (3) in the present invention are a compound which is multimerized, the compound becomes to have a high molecular weight, the intermolecular interaction becomes bigger and the volatility by heat decreases, and thus heat resistance is excellent. In addition, since a conjugated system is retained in the entire area of a structure of the compound, the compound has a characteristic which is excellent in light resistance due to being effectively able to relax a state which is excited by light energy by an extended conjugated system, and thus even in a case of using for a long time, an effect in which an ultraviolet ray shielding effect does not decrease and yellowing does not occur due to not decomposing can be obtained.

The ultraviolet absorbers represented by the general formulae (1) to (3) described above may be used as one kind only or can be used in combination of two or more kinds thereof.

Any form of use of the ultraviolet absorber of the present invention may be used. For example, a liquid dispersoid, a solution, a resin composition, and the like are included.

The maximum absorption wavelength of the ultraviolet absorber of the present invention is not particularly limited, however, is preferably from 250 nm to 400 nm, and is more preferably 280 nm to 380 nm. A half value width is preferably from 20 nm to 100 nm, and more preferably from 40 nm to 80 nm.

The maximum absorption wavelength and the half value width which are specified in the present invention can be easily measured by a person skilled in the art. The measurement method is described, for example, in "4th Edition Experimental Chemistry Course 7 Spectrum II" edited by The Chemical Society of Japan (MARUZEN Co., Ltd., 1992), pp. 180 to 186, or the like. Specifically, a sample is dissolved in a suitable solvent, the cell made of quartz or made of glass is used, two cells for sample and for reference are used, and the maximum absorption wavelength and half value width are measured by a spectrophotometer. It is required for a solvent which is used that a solvent does not have the absorption in a measurement wavelength region, the interaction with a solute molecule is small, the volatility is not too significant, or the like, in addition to the solubility of a sample. As long as the solvent is a solvent which is satisfied with the above conditions, it is possible to select an arbitrary one. In the present invention, ethyl acetate (EtOAc) is used as a solvent and the measurement is performed.

As to the maximum absorption wavelength and the half value width of the compound in the present invention, a solution having a concentration of approximately $5 \times 10^{-5}$ mol·dm$^{-3}$ is prepared using ethyl acetate as a solvent, and a value which is measured using a quartz cell with an optical path length of 10 mm is used.

The spectrum half value width is described, for example, in "4th Edition Experimental Chemistry Course 3 Basic Operation III" edited by The Chemical Society of Japan (MARUZEN Co., Ltd., 1991), p. 154, or the like. Moreover, the half value width is explained using an example in which the wavenumber scale is used for the horizontal axis in the book described above, however, as to the half value width in the present invention, a value in a case where the wavelength scale is used for the axis is used, and a unit of the half value width is nm. Specifically, the half value width indicates a width of an absorption band which is a half of the absorbance in the maximum absorption wavelength and is used as a value which indicates a shape of an absorption spectrum. A spectrum having small half value width is a sharp spectrum and a spectrum having large half value width is a broad spectrum. Since an ultraviolet ray absorption compound which gives a broad spectrum also has the absorption in a wide region on the long-wavelength side from the maximum absorption wavelength, an ultraviolet ray absorption compound having a spectrum having small half value width is preferable in order to effectively shield a long-wavelength ultraviolet ray region without the coloration of yellowish.

As described in "Chemistry Seminar 9 Color Chemistry" written by TOKITA Sumio (MARUZEN Co., Ltd., 1982), pp. 154 to 155, the strength of the light absorption, that is, an oscillator strength is proportional to the integral of the molar extinction coefficient, and when the symmetry of the absorption spectrum is good, the oscillator strength is proportional to multiplication of the absorbance and the half value width at the maximum absorption wavelength (however, the half value width in this case is a value where the wavelength scale is used for the axis). This means the absorbance becomes larger at the maximum absorption wavelength as to a compound having a spectrum having small half value width in a case where the values of the transition moment are the same. There is an advantage in which a region around the maximum absorption wavelength can be effectively shielded by using such an ultraviolet ray absorption compound in only a small amount, however, when the wavelength moves slightly away from the maximum absorption wavelength, the absorbance rapidly decreases, and thus a wide region can not be shielded.

As to the ultraviolet absorber, the molar extinction coefficient at the maximum absorption wavelength is preferably 20,000 or more, more preferably 30,000 or more, and particularly preferably 50,000 or more. If the molar extinction coefficient is 20,000 or more, since the absorption efficiency per mass of the ultraviolet absorber can be sufficiently obtained, the used amount of the ultraviolet absorber for completely absorbing an ultraviolet ray region can be reduced. This is preferable, from the viewpoint of preventing the skin irritation or the accumulation into living bodies and the point in which bleed-out is not likely to occur. Moreover, as to the molar extinction coefficient, a definition described in, for example, "New Experimental Chemistry Course 9 Analytical Chemistry [II]" edited by The Chemical Society of Japan (MARUZEN Co., Ltd., 1997), p. 244, or the like, is used, and when the maximum absorption wavelength and the half value width described above are determined, it is possible to determine the molar extinction coefficient together.

The ultraviolet absorber of the present invention (hereinafter, in some cases, simply referred to as an "ultraviolet absorber") can be also used in a state of a dispersoid in which the ultraviolet absorber is dispersed in a dispersive medium. Hereinafter, description will be given of an ultraviolet absorber dispersoid including the ultraviolet absorber of the present invention.

Any medium in which the ultraviolet absorber of the present invention is dispersed may be used. For example, water, an organic solvent, a resin, a solution of a resin, and the like are included. They may be used alone or may be used in combination.

As an organic solvent of a dispersive medium used in the present invention, for example, hydrocarbon-based such as pentane, hexane or octane, aromatic-based such as benzene, toluene or xylene, ether-based such as diethyl ether or methyl-t-butyl ether, alcohol-based such as methanol, ethanol or isopropanol, ester-based such as acetone, ethyl acetate or butyl acetate, ketone-based such as methyl ethyl ketone, nitrile-based such as acetonitrile or propionitrile, amide-based such as N,N-dimethylformamide, N,N-dimethylacetamide or N-methylpyrrolidone, sulfoxide-based such as dimethyl sulfoxide, amine-based such as triethylamine or tributylamine, carboxylic acid-based such as acetic acid or propionic acid, halogen-based such as methylene chloride or chloroform, heterocycle-based such as tetrahydrofuran or pyridine, and the like are included. It is also possible to use in combination thereof with an arbitrary ratio.

As a resin of a dispersive medium used in the present invention, a thermoplastics resin and a thermosetting resin used in manufacturing conventional well-known various compacts, sheets, films, or the like in the related art are included. As a thermoplastics resin, for example, a polyethylene-based resin, a polypropylene-based resin, a poly(meth) acrylic acid ester-based resin, a polystyrene-based resin, a styrene-acrylonitrile-based resin, an acrylonitrile-butadiene-styrene-based resin, a polyvinyl chloride-based resin, a polyvinylidene chloride-based resin, a polyvinyl acetate-based resin, a polyvinyl butyral-based resin, an ethylene-vinyl acetate-based copolymer, an ethylene-vinyl alcohol-based resin, a polyethylene terephthalate resin (PET), a polybutylene terephthalate resin (PBT), a liquid crystalline polyester resin (LCP), a polyacetal resin (POM), a polyamide resin (PA), a polycarbonate resin, a polyurethane resin, a polyphenylene sulfide resin (PPS), and the like are included, and they are used as one kind or as two or more kinds of polymer blends or polymer alloys. In addition, these resins are also used as a thermoplastic molding material in which a natural resin contains the fillers such as glass fiber, carbon fiber, half carbonized fiber, cellulose-based fiber or glass beads, a flame retardant, or the like. In addition, an additive agent for resin used in the related art, for example, polyolefin-based resin fine powder, polyolefin-based wax, ethylene bisamide-based wax, metal soap, or the like can be also used alone or in combination, as necessary.

As a thermosetting resin, for example, an epoxy resin, a melamine resin, an unsaturated polyester resin, and the like are included, and they can be also used as a thermosetting molding material containing the fillers such as glass fiber, carbon fiber, half carbonized fiber, cellulose-based fiber or glass beads or a flame retardant, in addition to a natural resin.

A dispersoid containing the ultraviolet absorber can be also used together with a dispersant, an anti-foam agent, a preservative, an antifreeze agent, a surfactant, or the like. In addition, an arbitrary compound may be included together. For example, a dye, a pigment, an infrared absorber, a fragrance, a polymerizable compound, a polymer, an inorganic substance, a metal, and the like are included.

As a device for obtaining a dispersoid containing the ultraviolet absorber of the present invention, a high speed stirring type disperser having large shear force, a disperser which gives an ultrasonic energy having high intensity, or the like can be used. Specifically, there are coloid mills, a homogenizer, a capillary type emulsification device, a liquid siren, an electromagnetic strain type ultrasonic generator, an emulsification device having a pohlman whistle, or the like. A preferred high speed stirring type disperser used in the present invention is a dispenser of a type in which a main part in which a dispersing action is performed is rotated with high speed (500 rpm to 15,000 rpm, preferably 2,000 rpm to 4,000 rpm) in a liquid, such as a dissolver, the Polytron, a homo mixer, a homo blender, the Kady mill, the Jet Ajiter, or the like. A high speed stiffing type disperser used in the present invention is also called as a dissolver or a high speed impeller disperser, and as also described in JP1980-129136A (JP-S55-129136A), one formed by alternately putting a saw-tooth shaped plate and an impeller that is vertically bended on an axis that rotates with high speed is also a preferred example.

When an emulsified dispersoid containing the ultraviolet absorber of the present invention is prepared, it is possible to follow various processes. For example, when the ultraviolet absorber is dissolved in an organic solvent, the ultraviolet absorber is dissolved in a mixture of one kind or two or more kinds of a plurality of arbitrary components arbitrarily selected from among a high boiling point organic solvent, a hydrophobic low boiling point organic solvent or a hydrophilic organic solvent, and next, it is dispersed in water or a hydrophilic colloidal aqueous solution in the presence of a surface active compound. A method of mixing a water-insoluble phase containing the ultraviolet absorber with an aqueous phase may be a so-called forward mixing method in which a water-insoluble phase is added into an aqueous phase under stirring, or a back mixing method which is opposite thereto.

In addition, the ultraviolet absorber of the present invention can be also used in a state of a solution dissolved in a medium in a liquid state. Hereinafter, description will be given of an ultraviolet absorber solution containing the ultraviolet absorber of the present invention.

Any liquid in which the ultraviolet absorber of the present invention is dissolved may be used. For example, water, an organic solvent, a resin, a solution of a resin, and the like are included. As an example of the organic solvent, the resin and the solution of the resin, ones described as the dispersion medium described above are included. They may be used alone or may be used in combination thereof.

In addition, the solution containing the ultraviolet absorber of the present invention may include an arbitrary compound together. For example, a dye, a pigment, an infrared absorber, a fragrance, a polymerizable compound, a polymer, an inorganic substance, a metal, and the like are included. They may not necessarily be dissolved except the ultraviolet absorber of the present invention.

The content of the ultraviolet absorber described above in the solution containing the ultraviolet absorber of the present invention can not be unambiguously determined since the content is different depending on the purpose of use and the form of use, however, the content may be an arbitrary concentration in accordance with the purpose of use. The content is preferably from 0.001% by mass to 30% by mass, and more preferably from 0.01% by mass to 10% by mass, with respect to the total amount of the solution. The solution having a high concentration is produced in advance and it is also possible to use by diluting when desired. As a diluting solvent, it is possible to arbitrarily select from organic solvents described above.

One which is stabilized by the ultraviolet absorber of the present invention includes a dye, a pigment, a food, a beverage, a body care product, a vitamin compound, a medicine, an ink, oil, fat, wax, a surface coating, a cosmetic, a photographic material, a fabric and a coloring matter thereof, a plastic material, a rubber, a coating, a resin composition, a polymeric additive agent, and the like.

An embodiment using the ultraviolet absorber of the present invention may be an embodiment using any method. The ultraviolet absorber of the present invention may be used alone or may be used as a composition, however, is preferably used as a composition. Among those, a resin composition containing the ultraviolet absorber of the present invention (hereinafter, also, referred to as a "resin composition of the present invention" or simply a "resin composition") is preferable. Hereinafter, description will be given of a resin composition containing the ultraviolet absorber of the present invention.

[Resin Composition]

The resin composition containing the ultraviolet absorber of present invention includes a resin. The resin composition containing the ultraviolet absorber of present invention may be formed by dissolving a resin in an arbitrary solvent.

The ultraviolet absorber of the present invention can be contained in the resin composition by various methods. In a case where the ultraviolet absorber of the present invention has a compatibility with the resin composition, the ultraviolet absorber of the present invention can be directly added to the resin composition. The ultraviolet absorber of the present invention is dissolved in an auxiliary solvent having a compatibility with the resin composition, and the solution thereof may be added to the resin composition. The ultraviolet absorber of the present invention is dispersed in a high boiling point organic solvent or a polymer, and the dispersoid thereof may be also added to the resin composition.

(High Boiling Point Organic Solvent)

The boiling point of the high boiling point organic solvent is preferably 180° C. or more, and further preferably 200° C. or more. The melting point of the high boiling point organic solvent is preferably 150° C. or less, and further preferably 100° C. or less. As an example of the high boiling point organic solvent, a phosphoric acid ester, a phosphonic acid ester, a benzoic acid ester, a phthalic acid ester, a fatty acid ester, a carbonic acid ester, an amide, an ether, a halogenated hydrocarbon, an alcohol, and paraffin are included. A phosphoric acid ester, a phosphonic acid ester, a phthalic acid ester, a benzoic acid ester and a fatty acid ester are preferable.

A method of adding the ultraviolet absorber of the present invention can be referred to each application of JP1983-209735A (JP-S58-209735A), JP1988-264748A (JP-S63-264748A), JP1992-191851A (JP-H04-191851A) and JP1996-272058A (JP-H08-272058A), and GB 2016017A.

(Resin)

Description will be given of a resin used in the resin composition. The resin may be either a natural or a synthetic polymer. For example, a polyolefin (for example, polyethylene, polypropylene, polyisobutylene, poly(1-butene), poly-4-methylpentene, polyvinylcyclohexane, polystyrene, poly(p-methylstyrene), poly($\alpha$-methylstyrene), polyisoprene, polybutadiene, polycyclopentene, polynorbornene, or the like), a copolymer of a vinyl monomer (for example, an ethylene/propylene copolymer, an ethylene/methylpentene copolymer, an ethylene/heptene copolymer, an ethylene/vinyl cyclohexane copolymer, or an ethylene/cycloolefin copolymer (for example, a cycloolefin copolymer such as ethylene/norbornene (COC: Cyclo-Olefin Copolymer)), a propylene/butadiene copolymer, an isobutylene/isoprene copolymer, an ethylene/vinylcyclohexene copolymer, an ethylene/alkyl acrylate copolymer, an ethylene/alkyl methacrylate copolymer, or the like), an acrylic-based polymer (for example, a polymethacrylate, a polyacrylate, a polyacrylamide, a polyacrylonitrile, or the like), polyvinyl chloride, polyvinylidene chloride, polyvinyl fluoride, polyvinylidene fluoride, a vinyl chloride/vinyl acetate copolymer, a polyether (for example, a polyalkylene glycol, a polyethylene oxide, a polypropylene oxide, or the like), a polyacetal (for example, polyoxymethylene), a polyamide, a polyimide, a polyurethane, a polyurea, a polyester (for example, polyethylene terephthalate, polyethylene naphthalate, polybutylene terephthalate, or the like), a polycarbonate, a polyketone, a polysulfone polyether ketone, a phenol resin, a melamine resin, a cellulose ester (for example, diacetyl cellulose, triacetyl cellulose (TAC), propionyl cellulose, butyryl cellulose, acetyl propionyl cellulose or nitrocellulose), a polysiloxane, a natural polymer (for example, cellulose, a rubber, gelatin, or the like), and the like are included.

A case in which the resin used in the present invention is a synthetic polymer is preferable, and a polyolefin, an acrylic-based polymer, a polyester, a polycarbonate and a cellulose ester are more preferable. Among those, polyethylene, polypropylene, poly (4-methylpentene), polymethyl methacrylate, polycarbonate, polyethylene terephthalate, polyethylene naphthalate, polybutylene terephthalate and triacetyl cellulose are particularly preferable.

The resin used in the present invention is preferably a thermoplastics resin.

In the present invention, as an ultraviolet absorber, two or more kinds of compounds which have different structures and are represented by the general formulae (1) to (3) described above may be used together. In addition, the compounds represented by the general formulae (1) to (3) described above may be used together with one or more kinds of ultraviolet absorbers having structures aside from these. When two kinds (preferably three kinds) of ultraviolet absorbers in which the basic skeleton structures are different are used together, it is possible to absorb an ultraviolet ray having a wide wavelength region. In addition, when two or more kinds of ultraviolet absorbers are used together, there is also a function in which a dispersion state of the ultraviolet absorber becomes stabilized. Any ultraviolet absorber having a structure except the general formulae (1) to (3) described above can be used, and compounds such as triazine-based, benzotriazole-based, benzophenone-based, merocyanine-based, cyanine-based, dibenzoylmethane-based, cinnamic acid-based, cyanoacrylate-based, benzoic acid ester-based are included. For example, the ultraviolet absorbers described in Fine Chemical, 2004, the May issue, pp. 28 to 38, "New Development of Functional Additive Agent for Polymer" published by Toray Research Center, Investigation Research Department (Toray Research Center, Inc., 1999), pp. 96 to 140, and "Development of Polymer Additive Agent and Environmental Measure" supervised by OKATSU Yasukazu (CMC Publishing Co., Ltd., 2003), pp. 54 to 64, or the like are included.

As an ultraviolet absorber having a structure except the general formulae (1) to (3) described above, a benzotriazole-based compound, a benzophenone-based compound, a salicylic acid-based compound, a benzoxazinone-based compound, a cyanoacrylate-based compound, a benzoxazole-based compound, a merocyanine-based compound and a triazine-based compound are preferable. A benzoxazinone-based compound, a benzotriazole-based compound, a benzophenone-based compound and a triazine-based compound are more preferable. A benzoxazinone-based compound is particularly preferable. The ultraviolet absorber having a structure except the general formula (1) described above is described in detail in paragraph numbers [0117] to [0121] in JP2008-273950A, and a material described in the application described above can be also applied to the present invention.

As described above, in the present invention, it is preferred to use in combination of the compounds represented by the general formulae (1) to (3) with a benzoxazinone-based compound. Since the compounds represented by the general formulae (1) to (3) also have excellent light resistance in a long wavelength region, an effect of preventing a deterioration of benzoxazinone capable of shielding up to longer wavelength region is achieved, and it is possible to continue an effect of shielding up to longer wavelength region for a long time by using together with a benzoxazinone-based compound, and it is therefore preferable.

In the present invention, while it is possible to obtain a practically sufficient ultraviolet ray shielding effect using only ultraviolet absorber of the present invention, in a case where the strictness is further required, a white pigment having a strong hiding power, for example, a titanium oxide or the like may be used together. In addition, when the outside appearance and the color tone become a problem, or depending on the preference, a trace of (0.05% by mass or less with respect to the mass of the resin) coloring agent can be used together. In addition, a fluorescent brightening agent may be used together, with respect to an application in which it is important to be transparence or white. As a fluorescent brightening agent, a commercially available one, the general formula [1] and specific compound examples 1 to 35 described in JP2002-53824A, and the like are included.

As to the ultraviolet absorber of the present invention, an arbitrary amount which is required for imparting the desired performance can be contained. These amounts are different, depending on the compounds or the resins which are used, however, it is possible to appropriately determine the content rate. The content rate is preferably more than 0% by mass and 20% by mass or less, more preferably more than 0% by mass and 10% by mass or less, and further preferably from 0.05% by mass or more 5% by mass or less, in the total mass of the resin composition. If the content rate is in the range described above, it is possible to obtain a sufficient ultraviolet ray shielding effect and suppress bleed-out, and it is therefore preferable.

The resin composition of the present invention may appropriately contain an arbitrary additive agent such as an anti-oxidant, a light stabilizer, a processing stabilizer, an age inhibitor or a compatibilizer, as necessary, in addition to the resin and the ultraviolet absorber described above and an ultraviolet stabilizer.

The resin composition containing the ultraviolet absorber of the present invention can be used for all applications in which a synthetic resin is used, however, it is possible and particularly suitable use it for an application in which there is some possibility of being exposed to particularly sunlight or light containing an ultraviolet ray. As specific examples, for example, a glass substitute, a surface coating material thereof, a window glass of residence, facility, transportation equipment or the like, a coating material for daylight glass and light source protective glass, a window film of residence, facility, transportation equipment or the like, an interior and exterior material of residence, facility, transportation equipment or the like, and a coating for interior and exterior and a coating film formed by the coating, an alkyd resin lacquer coating and a coating film formed by the coating, an acrylic lacquer coating and a coating film formed by the coating, a member for light source such as a fluorescent lamp or a mercury lamp which emits an ultraviolet ray, a member for precision machine or electronic and electric equipment, a material for blocking electromagnetic waves or the like generated by various displays, a container or a packaging material of a food, a chemical good, a drug or the like, a compact disk coat for special packaging of a bottle, a box, a blister or a cup, a sheet or a film material for agricultural industry, an anti-fading agent for printed matter, dye good, dye and pigment or the like, a protective film for polymer support (for example, for component made of plastic such as a machine or an automobile component), a printed matter over coat, an ink jet medium film, a laminated frosting, an optical light film, a safety glass/a front glass intermediate layer, an electrochromic/photochromic application, an over laminated film, a solar heat control film, a cosmetic such as a suntan cream, a shampoo, a rinse or a hair dressing, a fiber product and a fiber for clothing such as a sport ware, a stocking or a hat, an interior equipment for home such as a curtain, a carpet or a wall paper, a medical instrument such as a plastic lens, a spectacle lens, a contact lens or an artificial eye, an optical good such as an optical filter, a back light display film, a prism, a mirror or a photographic material, a film for die, a transfer type sticker, a film for preventing scribbling, a stationery such as a tape or an ink, a sign board, an indicator or the like and a surface coating material thereof, and the like are included.

As a shape of a resin molded article formed by the resin composition of the present invention, any shape such as a flat membrane type, a powder type a spherical type particle, a crushed particle, a lump type continuous body, a fiber type, a tubular type, a hollow fiber type, a granular type, a plate type or a porous type may be used.

Since the ultraviolet absorber of the present invention is contained in the resin composition, the resin composition of the present invention has excellent light resistance (ultraviolet light fastness) and a precipitation of the ultraviolet absorber or bleed-out due to using for a long time does not occur. In addition, since the resin composition of the present invention has excellent long wavelength ultraviolet ray absorption ability, it is possible to use as an ultraviolet ray absorbing filter or a container and also protect a compound or the like which is weak to an ultraviolet ray. For example, by molding the resin described above by an arbitrary method such as an extrusion molding or an injection molding, a resin molded article formed by the resin composition of the present invention (a container or the like) can be obtained. In addition, by applying the solution of the resin described above to a resin molded article which is separately produced and drying, it is also possible to obtain a molded article coated by an ultraviolet ray absorbing film formed by the resin composition of the present invention.

In a case where the resin composition of the present invention is used as an ultraviolet ray absorbing filter or an ultraviolet ray absorbing filter, it is preferred that the resin be transparent. As an example of the transparent resin, a cellulose ester (example, diacetyl cellulose, triacetyl cellulose (TAC), propionyl cellulose, butyryl cellulose, acetyl propionyl cellulose or nitrocellulose), a polyamide, a polycarbonate, a polyester (example, polyethylene terephthalate, polyethylene naphthalate, polybutylene terephthalate, poly-1,4-cyclohexanedimethylene terephthalate, polyethylene-1,2-diphenoxyethane-4,4'-dicarboxylate or polybutylene terephthalate), a polystyrene (example, syndiotactic polystyrene), a polyolefin (example, polyethylene, polypropylene or polymethyl pentene), a (meth)acrylic resin, a syndiotactic polystyrene, a polysulfone, a polyether sulfone, a polyether ketone, a polyether imide, a polyoxy ethylene, and the like are included. A cellulose ester, a polycarbonate, a polyester, a polyolefin and a polymethyl methacrylate are preferable, and a polycarbonate and a polyester are more preferable. A polyester is further preferable, and polyethylene terephthalate is particularly preferable. Here, a (meth)acrylic resin means at least one of a methacrylic resin and an acrylic resin. A resin molded article obtained by the resin composition of the present invention can be also used as a transparent support, and the light transmittance of a transparent support is preferably 80% or more, and further preferably 86% or more.

In the present invention, a matter described in paragraph numbers [0192] to [0230] in JP2009-209343A can be applied.

Description will be given of a packaging material including the ultraviolet absorber of the present invention. The packaging material including the ultraviolet absorber of the present invention may be a packaging material consisting of any kind of polymers as long as the packaging material includes the compounds represented by the general formulae (1) to (3) described above. For example, a thermoplastics resin, a polyvinyl alcohol, a polyvinyl chloride, a polyester, a heat shrinkable polyester, a styrene-based resin, a polyolefin, ROMP and the like are included. For example, the packaging material may be a resin having an evaporated thin film layer of an inorganic substance. For example, the packaging material may be a paper on which a resin including the ultraviolet absorber is applied.

The packaging material including the ultraviolet absorber of the present invention may be one which packages any matter such as a foodstuff, a beverage, a pharmaceutical, a cosmetic or a personal care product. For example, a food packaging, a colored liquid packaging, a packaging for liquid preparation, a medicine container packaging, a sterilized packaging for medicine, a packaging of sensitive material for photography, a photographic film packaging, a packaging for ultraviolet ray curable type ink, a shrinkable label and the like are included.

The packaging material including the ultraviolet absorber of the present invention may be, for example, a transparent package body or may be a light blocking package body.

The packaging material including the ultraviolet absorber of the present invention, for example, not only may have an ultraviolet ray shielding property, but also may have another performance together. For example, one having a gas barrier property together, one including an oxygen indicator, one combining the ultraviolet absorber with a fluorescent brightening agent, and the like are included.

The packaging material including the ultraviolet absorber of the present invention may be manufactured using any method. A method of forming an ink layer, a method of laminating a resin containing an ultraviolet absorber by a melt extrusion, a method of coating on a substrate film, a method of dispersing an ultraviolet absorber in an adhesive agent, and the like are included.

Description will be given of a container including the ultraviolet absorber of the present invention. The container including the ultraviolet absorber of the present invention may be a container consisting of any kind of polymers as long as the container includes the compounds represented by the general formulae (1) to (3) described above. For example, a thermoplastics resin container, a container made of polyester, a container made of polyethylene naphthalate, a container made of polyethylene, a container made of a cyclic olefin-based resin composition, a plastic container, a transparent polyamide container, and the like are include. For example, the container may be a paper container including a resin. The container may be a glass container having an ultraviolet ray absorbing layer.

An application of the container including the ultraviolet absorber of the present invention may be one into which any of a foodstuff, a beverage, a pharmaceutical, a cosmetic, a personal care product, a shampoo, or the like is put. A liquid fuel storing container, a golf ball container, a container for foodstuff, a container for alcohol, a pharmaceutical filling container, a beverage container, a container for oily foodstuff, a container for solution for analytical reagent, an instant noodles container, a light resistance cosmetic material container, a medicine container, a container for high purity chemical liquid, a container for liquid agent, a container for ultraviolet ray curable type ink, a W plastic ampule, and the like are included.

The container including the ultraviolet absorber of the present invention may have not only an ultraviolet ray blocking property, and but also may have another performance together. For example, an antibacterial container, a flexible container, a dispenser container, a biodegradable container, and the like are included.

The container including the ultraviolet absorber of the present invention may be manufactured using any method. For example, a method by a two layer stretch blow molding, a multilayer co-extrusion blow molding method, a method of forming an ultraviolet ray absorbing layer outside of a container, a method using a shrinkable film, a method using a supercritical fluid, and the like are included.

Description will be given of a coating and a coating film including the ultraviolet absorber of the present invention. The coating including the ultraviolet absorber of the present invention may be a coating consisting of any component as long as the coating includes the compounds represented by the general formulae (1) to (3) described above. For example, coatings consisting of components such as acrylic resin-based, urethane resin-based, amino alkyd resin-based, epoxy resin-based, silicone resin-based, fluorine resin-based are included. These resins can be arbitrarily blended with a main agent, a curing agent, a diluent, a leveling agent, a cissing inhibitor, or the like.

For example, in a case where an acrylic urethane resin or a silicon acrylic resin is selected as a transparent resin component, polyisocyanate or the like can be used as a curing agent, and a hydrocarbon-based solvent such as toluene or xylene, an ester-based solvent such as isobutyl acetate, butyl acetate or amyl acetate, or an alcohol-based solvent such as isopropyl alcohol or butyl alcohol can be used as a diluent. In addition, here, the acrylic urethane resin means an acrylic urethane resin which is obtained by a reaction of a methacrylic acid ester (typically, methyl), a hydroxyethyl methacrylate copolymer and a polyisocyanate. Moreover, in this case, the polyisocyanate includes tolylene diisocyanate, diphenylmethane diisocyanate, polymethylene polyphenylene polyisocyanate, tolidine diisocyanate, naphthalene diisocyanate, hexamethylene diisocyanate, isophorone diisocyanate, xylylene diisocyanate, dicyclohexyl methane diisocyanate, hexamethylene diisocyanate, and the like. As other transparent resin components, for example, polymethyl methacrylate, a polymethyl methacrylate styrene copolymer, polyvinyl chloride, polyvinyl acetate, and the like are included. Furthermore, a levelling agent such as an acrylic resin or a silicone resin, cissing inhibitor such as a silicone-based, or an acrylic-based, or the like can be blended, as necessary, in addition to these components.

The purpose of use of a coating including the ultraviolet absorber of the present invention may be for any application. For example, an ultraviolet ray shielding coating, an ultraviolet ray and near infrared ray blocking coating, a coating for shielding electromagnetic waves, a clear coating, a metallic coating composition, a cationic electrodeposition coating, an antibacterial and unleaded cationic electrodeposition coating, a powder coating, an aqueous intermediate coating paint, an aqueous metallic coating, an aqueous clear coating, a coating for top coat which is used for an automobile, a building and a civil engineering product, a curable coating, a coating film forming composition which is used for a plastic material or the like such as a car bumper, a coating for metallic plate, a cured gradient coating film, a coating material for electrical wire, an automobile repairing coating, an anionic electrodeposition coating, a coating for automobile, a coating for coated steel plate, a coating for stainless steel, a insecticidal coating for lamp, an ultraviolet ray curable type coating, a special antibacterial coating, a coating for preventing asthenopia, a defogging coating, a super-weather resistance coating, a gradient coating, a photocatalytic coating, a peelable coating, a coating for separating a concrete, an anticorrosive coating, a protective coating, a water repellency protective coating, a coating for plate glass scattering prevention, an alkali-soluble type protective coating, an aqueous temporary protective coating composition, a coating for floor, an emulsion coating, a two-pack type aqueous coating, a one-pack coating, a UV curable coating, an electron beam curable type coating composition, a thermosetting coating composition, an aqueous coating for stoving lacquer, a powder coating and a slurry coating, a coating for repair, a powder coating aqueous dispersoid, a coating for plastic, an electron beam curable type coating, and the like are included.

The coating including the ultraviolet absorber of the present invention is generally configured by a coating (including a transparent resin component as a main component) and an ultraviolet absorber, however, the content of the ultraviolet absorber is preferably 20 parts by mass or less, with respect to the total mass of the transparent resin component. The thickness when applying is preferably from 2 μm to 1,000 μm, and further preferably between 5 μm and 200 μm. Methods of applying these coatings are arbitrary, however, there are a spraying method, a dipping method, a roller coat method, a flow coater method, a flow coating method, and the like. Drying after application varies depending on the coating components, however, basically, drying is preferably performed from room temperature to 120° C. for approximately 10 minutes to 90 minutes.

The coating film including the ultraviolet absorber of the present invention is a coating film including the ultraviolet absorber consisting of the compounds represented by the general formulae (1) to (3) described above and a coating film formed by using the coating described above including the ultraviolet absorber of the present invention.

Description will be given of an ink including the ultraviolet absorber of the present invention. The ink including the ultraviolet absorber of the present invention may be an ink having any form as long as the ink is one including the compounds represented by the general formulae (1) to (3) described above. For example, dye ink, pigment ink, aqueous ink, oil ink, and the like are included. In addition, they may be use for any application. For example, screen printing ink, flexographic printing ink, gravure printing ink, lithographic offset printing ink, letterpress printing ink, UV ink, EB ink, and the like are included. In addition, for example, ink jet ink photochromic ink, thermal transfer ink, masking ink, security ink, DNA ink, and the like are also included.

Any form obtained by using an ink including the ultraviolet absorber of the present invention is included in the present invention. For example, a printed matter, a laminated body obtained by laminating the printed matter, a packaging material or a container using the laminated body, an ink receiving layer, and the like are included.

Description will be given of a fiber including the ultraviolet absorber of the present invention. The fiber including the ultraviolet absorber of the present invention may be a fiber consisting of any kind of resins as long as the fiber is one including the compounds represented by the general formulae (1) to (3) described above. For example, polyester fiber, polyphenylene sulfide fiber, polyamide fiber, aramid fiber, polyurethane fiber, cellulose fiber, and the like are included.

The fiber including the ultraviolet absorber of the present invention may be manufactured by any method. For example, the resin including the compounds represented by the general formulae (1) to (3) described above in advance may be processed into a fiber type and, for example, a treatment may be performed by using a solution or the like including the compounds represented by the general formulae (1) to (3) described above, with respect to one in which the resin is processed into a fiber type. A treatment may be performed by using a supercritical fluid.

The fiber including the ultraviolet absorber of the present invention can be used for various applications. For example, a clothing, a lining, an underwear, a blanket, socks, artificial leather, an insecticidal mesh sheet, a mesh sheet for construction, a carpet, a special moisture permeable and waterproof sheet, a non-woven fabric, a sheet-like material consisting of ultrafine fibers or fibers, a refreshing clothing moisture permeable and waterproof sheet, a flame retardant artificial suede like structure, a resin tarpaulin, a film agent, an external wall material agent, a house for agriculture, a net for construction material, a mesh, a filter base material, an antifouling film agent, a mesh textile, a land net, an underwater net, ultrafine fibers, textile fibers, a base fabric for airbag, an ultraviolet ray absorbing fiber product, and the like are included.

Description will be given of a building material including the ultraviolet absorber of the present invention. The building material including the ultraviolet absorber of the present invention may be a building material consisting of any kind of polymers as long as the building material is one including the compounds represented by the general formulae (1) to (3) described above. For example, polymers such as vinyl chloride-based, olefin-based, polyester-based, polyphenylene ether-based, polycarbonate-based are included.

The building material including the ultraviolet absorber of the present invention may be manufactured by any method. For example, the building material may be formed into the desired shape by using a material including the compounds represented by the general formulae (1) to (3) described above, may be formed by laminating a material including the compounds represented by the general formulae (1) to (3) described above, may be formed by forming a coating layer using the compounds represented by the general formulae (1) to (3) described above, and may be formed by painting a coating containing the compounds represented by the general formulae (1) to (3) described above.

The building material including the ultraviolet absorber of the present invention can be used for various applications. For example, a building material for exterior, a woody structural body for building material, a roof material for building material, an antibacterial building material, a base material for building material, an antifouling building material, a flame retardant material, a ceramic industry-based building material, a building material for decoration, a coated article for building material, a decorative material, a net for building material, a moisture permeable and waterproof sheet for building material, a mesh sheet for construction work, a film for building material, a film for mounting, a coating material for building material, an adhesive agent composition for building material, a civil engineering and construction structure, a coating material for walking way, a sheet-like photo-curable resin, a protective coating for wood, a cover for push-button switch, a joining sheet agent, a wall paper, polyester film for mounting, a polyester film for mounting on molded member, a flooring material, and the like are included.

Description will be given of a recording medium including the ultraviolet absorber of the present invention. The recording medium including the ultraviolet absorber of the present invention may be a recording medium as long as the recording medium is a recording medium including the compounds represented by the general formulae (1) to (3) described above. For example, an ink jet recording medium, an image receiving sheet for sublimation transfer, an image recording medium, a thermal recording medium, a reversible thermal recording medium, an optical information recording medium, and the like are included.

Description will be given of an image display device including the ultraviolet absorber of the present invention. The image display device including the ultraviolet absorber of the present invention may be any image display device as long as the image display device is an image display device including the compounds represented by the general formulae (1) to (3) described above. For example, an image display device using an electrochromic element, an image display device a so-called electronic paper, a plasma display, an image display device using an organic EL element, and the like are included. The ultraviolet absorber of the present invention, for example, may be used for forming an ultraviolet ray absorbing layer in a laminated structure or may be used by being contained in a member such as a circular polarization plate which is required.

Description will be given of a cover for solar cell including the ultraviolet absorber of the present invention. The solar cell which can be applied may be a solar cell consisting of elements of any form such as a crystal silicon solar cell, an amorphous silicon solar cell or a dye sensitized solar cell. In a crystal silicon solar cell or an amorphous silicon solar cell, a cover material is used as a protective member which imparts the antifouling property, shock resistance or durability. In addition, in a dye sensitized solar cell, since a metal oxide-based semiconductor which becomes activated by being excited by light (particularly, an ultraviolet ray) is used as an electrode material, there is a problem in which a dye adhered as a photosensitizer deteriorates and the light power generation efficiency gradually decreases, and thus it has been proposed that an ultraviolet ray absorbing layer is provided.

The cover for solar cell including the ultraviolet absorber of the present invention may be one consisting of any kind of polymers. For example, a polyester, a thermosetting transparent resin, an α-olefin polymer, polypropylene, polyethersulfone, an acrylic resin, a transparent fluorine-based resin, and the like described in JP2006-310461A are included.

The cover for solar cell including the ultraviolet absorber of the present invention may be manufactured by any method. For example, an ultraviolet ray absorbing layer may be formed, layers including the ultraviolet absorber are respectively laminated, the cover for solar cell may be included in a resin of a filling material layer, and a film may be formed from a polymer including the ultraviolet absorber.

The cover for solar cell including the ultraviolet absorber of the present invention may have any form. A film, a sheet, a laminated film, a cover glass structure, and the like are included. For example, a front sheet, a back sheet, and the like are included. The cover for solar cell may be one in which the ultraviolet absorber is included in a sealing material.

Description will be given of a glass and a glass coating film including the ultraviolet absorber of the present invention. The glass and the glass coating film including the ultraviolet absorber of the present invention may have any form as long as the glass and a glass coating film are ones including the compounds represented by the general formulae (1) to (3) described above. In addition, they may be used for any application. For example, a heat ray blocking glass window glass, a colored glass, an ultraviolet ray sharp cut glass for high luminance light source such as a mercury lamp or a metal halide lamp, a frit glass, an ultraviolet ray blocking glass for vehicle, a colored heat ray absorbing glass, a fluorescent brightening agent containing ultraviolet ray absorbing and heat insulation glass, an ultraviolet ray and heat ray blocking glass for automobile, a stained glass for exterior, an ultraviolet ray and infrared ray absorbing glass having water repellent, a glass for head-up display device for vehicle, a dimming and heat blocking multilayer window, an ultraviolet ray and infrared ray cut glass, an ultraviolet ray cut glass, an ultraviolet ray and infrared ray absorbing glass for window, an ultraviolet ray blocking and antifouling film for window, a translucent panel for cultivation chamber, an ultraviolet ray and infrared ray absorbing glass having low permeation, a glass having low reflectivity and low transmittance, an edge light device, a roughened surface forming plate glass, a laminated glass for display, a glass with a conductive film, a antiglare glass, an ultraviolet ray and infrared ray absorbing glass having medium transparency, a window glass for privacy protection for vehicle, an antifogging glass for vehicle, a glass for paving material, a glass plate having the water drop adhesion preventive property and the heat ray blocking property, an ultraviolet ray and infrared ray absorbing bronze glass, a laminated glass, a glass with ID identification function, an optical filter for PDP, a skylight, and the like are included. The glass including the ultraviolet absorber of the present invention may be manufactured by any method.

In addition, as other usage examples, a light source cover for lightning device, artificial leather, a sport goggle, a deflection lens, a hard coat for various plastic products, a hard coat for putting onto the outside of the window, a window coating film, a highly accurate antiglare hard coat film, an antistatic hard coat film, a permeable hard coat film, a forgery protection slip described in JP2002-113937A, a purple patch inhibitor of turf, a sealing agent for joining a resin film sheet, a light guide body, a coating agent for rubber, a covering material for agriculture, a dyed candle, a rinse agent composition for cloth, a prism sheet, a special protective layer transfer sheet, a photocurable resin product, a sheet for floor, a light blocking printing label, an oil filler cup, a hard coating film coated article, an intermediate transfer recording medium, artificial hair, a low temperature heat shrinkable film for label, a fishing gear, microbeads, a precoated metal plate, a thin film, a heat shrinkable film, a label for in-mold forming, a projection screen, a decorative sheet, a hot melt adhesive agent, an adhesive agent, an electrodeposition coat, a base coat, a wood surface protective, a dimming material, a dimming film, a dimming glass, a moth-repelling lamp, a touch panel, a polycarbonate film covering, an optical fiber tape, solid wax, and the like are included.

Next, description will be given of a method for evaluating light resistance of a polymer material. As a method for evaluating light resistance of a polymer material, descriptions of "Approach for Photo-stabilization of Polymers" (CMC Publishing CO., LTD., 2000), pp. 85 to 107, "Foundation and Physical Properties of High Efficient Paint" (CMC Publishing CO., LTD., 2003), pp. 314 to 359, "Durability of Polymeric Materials and Composite Articles" (CMC Publishing CO., LTD., 2005), "Prolong of Lifetime and Environmental Measures for Polymeric Materials" (CMC Publishing CO., LTD., 2000), "Plastics Additives Handbook $5^{th}$ Edition" edited by H. Zweifel (Hanser Publishers), pp. 238 to 244, "Basic Course 2 Science of Plastic Packaging Container" written by KATSURA Tadahiko (The Society of Packaging Science & Technology, Japan, 2003), Chapter 8, and the like can be referred.

In addition, as an evaluation with respect to each application, it is possible to achieve by the following well-known evaluation methods. The deterioration by light in a polymer material can be evaluated by methods of JIS-K7105: 1981, JIS-K7101: 1981, JIS-K7102: 1981, JIS-K7219: 1998, JIS-K7350-1: 1995, JIS-K7350-2: 1995, JIS-K7350-3: 1996 and JIS-K7350-4: 1996 and methods with reference thereto.

Light resistance in a case of using as an application of a packaging and a container can be evaluated by a method of JIS-K7105: 1981 and methods with reference thereto. As a specific example thereof, the evaluation of the light transmittance and the transparency of a bottle body, the sensory test evaluation of a bottle content after ultraviolet ray exposure using a xenon light source, the evaluation of the haze value after irradiation using a xenon lamp, the evaluation of the haze value using a halogen lamp light source, the evaluation of the degree of yellowing using the blue wool scale after mercury lamp exposure, the evaluation of the haze value using a sunshine weatherometer, the visual evaluation of the colorability, the evaluation of the ultraviolet ray transmittance, the evaluation of the ultraviolet ray blocking rate, the evaluation of the light transmittance, the evaluation of the viscosity of an ink in an ink container, the visual inspection of a sample in a container after sunlight exposure, the evaluation of the color difference $\Delta E$, the evaluation of the ultraviolet ray transmission after irradiation using a white fluorescent lamp, the evaluation of the optical transmission, the evaluation of the color difference, the evaluation of the haze value, the evaluation of the color tone, the evaluation of the degree of yellowness, the evaluation of the light blocking property, the evaluation of the brightness using the color difference formula of the L* a* b* color system, the evaluation of yellow tint in samples after exposure for each wavelength after a xenon light is diffracted using the color difference $\Delta E$ a* b*, the evaluation of the ultraviolet ray absorption rate after ultraviolet ray exposure, the evaluation of the film tensile elongation after exposure using a sunshine weatherometer, the evaluation of the antimicrobial property after exposure using a xenon weatherometer, the evaluation of the color fading property of a packaging content after irradiation using a fluorescent lamp, the evaluation of the peroxide value of oil with respect to a salad oil filling bottle after exposure using a fluorescent lamp, the evaluation of the absorbance difference after irradiation using a chemical lamp, the surface glossiness retention ratio after exposure using a sunshine weatherometer, the appearance evaluation, the color difference after exposure using a sunshine weatherometer, the evaluation of the bending strength, the evaluation of the light blocking rate, the evaluation of the production amount of the peroxide in kerosene, and the like are included.

The long-period durability in a case of using as an application of a coating and a coating film can be evaluated by methods of JIS-K5400, JIS-K5600-7-5: 1999, JIS-K5600-7-6: 2002, JIS-K5600-7-7: 1999, JIS-K5600-7-8: 1999 and JIS-K8741 and methods with reference thereto. As a specific example thereof, the evaluation using the color concentration, the color difference $\Delta E$ a* b* in the CIE L* a* b* color coordinate and the residual glossiness after exposure by a xenon light resistance testing machine and an UVCON device, the evaluation of the absorbance with respect to a film on a quartz slide after exposure using a xenon arc light resistance testing machine, the evaluation using the color concentration and the color difference $\Delta E$ a* b* in the CIE L* a* b* color coordinate in wax after exposure using a fluorescent lamp and a UV lamp, the evaluation of the hue after exposure using a metal weather weather-resistance testing machine, the evaluation of the glossiness retention ratio and the evaluation using the color difference $\Delta E$ a* b* after the exposure test using a metal halide lamp, the evaluation of the feeling of glossiness after exposure using a sunshine carbon arc light source, the evaluation using the color difference $\Delta E$ a* b* after exposure using a metal weather weather-resistance testing machine, the glossiness retention ratio, the appearance evaluation, the evaluation of the glossiness retention ratio after exposure using a sunshine weatherometer, the evaluation using the color difference $\Delta E$ a* b* after exposure using a QUV weather-resistance testing machine, the evaluation of the glossiness retention ratio, the appearance evaluation with respect to a coated plate after exposure using a sunshine weatherometer, the evaluation of the change in the glossiness retention ratio and the evaluation of the change in the lightness values after exposure using a sunshine weatherometer, the appearance evaluation in a deterioration state of a coating film after exposure by the Dew-Cycle WOM with respect to a coating film, the evaluation of the ultraviolet ray transmittance of a coating film, the evaluation of the ultraviolet ray blocking rate of a coating film, the evaluation of the comparison of time in which the glossiness retention ratio of a coating film becomes 80% using a sunshine weatherometer, the evaluation of the rust formation after exposure using a Dew panel optical control weatherometer, the evaluation of the strength of the concrete with respect to a painted formwork after outdoor exposure, the evaluation using the color difference ΔE a* b* after outdoor exposure, the evaluation of cross-cut adhesion, the surface appearance evaluation, the evaluation of the glossiness retention ratio after outdoor exposure, the evaluation of the degree of yellowing (ΔYI) after exposure using a carbon arc light source, and the like are included.

Light resistance in a case of using as an application of an ink can be evaluated by methods of JIS-K5701-1: 2000, JIS-K7360-2 and ISO105-B02 and methods with reference thereto. Specifically, the evaluation by measuring the color concentration and the CIE L* a* b* color coordinate after exposure using a fluorescent lamp for office and a color fading testing machine, the evaluation of the electrophoresis after ultraviolet ray exposure using a xenon arc light source, the evaluation of the concentration of a printed matter by a xenon fadeometer, the evaluation of the ink dislocation property using a 100 W chemical lamp, the evaluation of the residual ratio of the dye at an image forming part by using a sunshine weatherometer, the evaluation of chalking and the evaluation of the discoloration of a printed matter using the EYE Super UV tester, the evaluation using the color difference ΔE a* b* in the CIE L* a* b* color coordinate as to a printed matter after exposure using a xenon fadeometer, the evaluation of the reflectance after exposure using a carbon arc light source, and the like are included.

Light resistance of a solar cell module can be evaluated by methods of JIS-C8917: 1998 and JIS-C8938: 1995 and methods with reference thereto. Specifically, the evaluation of the I-V measuring light power generation efficiency after exposure by a light source in which a correction filter for solar light simulation is installed in a xenon lamp, the evaluation of the grade of the gray scale for discoloration, the color evaluation and the appearance adhesion evaluation after exposure using a sunshine weatherometer and a fadeometer, and the like are included.

Light resistance of a fiber and a fiber product can be evaluated by methods of JIS-L1096: 1999, JIS-A5905: 2003, JIS-L0842, JIS-K6730, JIS-K7107, DIN75.202, SAEJ1885, SN-ISO-105-B02, and AS/NZS4399 and methods with reference thereto. The evaluation of the ultraviolet ray transmission, the evaluation of the blue scale for discoloration after exposure using a xenon light source and a carbon arc light source, the evaluation of the UV elimination ratio, the evaluation of the ultraviolet ray blocking property, the evaluation of the blue scale for discoloration after exposure using a carbon arc light source after dry cleaning, the evaluation of the color difference ΔE* based on the luminosity index and the psychometric chroma coordinates after exposure using a fadeometer, the evaluation of the tensile strength after exposure using a UV tester and a sunshine weatherometer, the evaluation of the total transmittance, the evaluation of the strength retention ratio, the evaluation of the ultraviolet ray protection factor (UPF), the evaluation of the gray scale for discoloration after exposure using a fadeometer at high temperature, the appearance evaluation after outdoor exposure, the evaluation of the degree of yellowness (YI) and the degree of yellowing (ΔYI) after ultraviolet ray exposure, the evaluation of the luminance factor, and the like are included.

Light resistance of a building material can be evaluated by methods of JIS-A1415: 1999 and methods with reference thereto. Specifically, the evaluation of the surface color tone after exposure using a sunshine weatherometer, the appearance evaluation after exposure using a carbon arc light source, the appearance evaluation after exposure using the EYE Super UV tester, the evaluation of the absorbance after exposure, the evaluation of the chromaticity and the color difference after exposure, the evaluation using the color difference ΔE a* b* in the CIE L* a* b* color coordinate after exposure using a metal halide lamp light source, the evaluation of the glossiness retention ratio, the evaluation of the change in the haze value after exposure using a sunshine weatherometer described in JP1998-44352A (JP-H10-44352A) and JP2003-211538A, the evaluation of the elongation retention ratio after exposure using a tension testing machine, the evaluation of the ultraviolet ray transmittance after immersing in a solvent using an ultraviolet visible light spectrophotometer, the visual evaluation of the appearance after exposure using the EYE Super UV tester, the evaluation of the change in the glossiness ratio after a QUV test, the evaluation of the glossiness retention ratio after exposure using a sunshine weatherometer, the evaluation using the color difference ΔE a* b* after ultraviolet ray exposure using a black light blue fluorescent lamp, the evaluation of the adhere retention ratio after exposure using an UVCON accelerated test machine, the evaluation of the ultraviolet ray blocking property, the appearance evaluation after outdoor exposure (JIS-A1410), the evaluation of the total light transmittance, the evaluation of the change in the haze, the evaluation of the tensile shear bond strength, the evaluation of the total light transmittance after exposure using a xenon weatherometer, the evaluation of the haze, the evaluation of the degree of yellowing, the degree of yellowing (ΔYI) after exposure using a sunshine weatherometer, the evaluation of the residual ratio of an ultraviolet absorber, and the like are included.

Light resistance in a case of using as an application of a recording medium can be evaluated by methods of JIS-K7350: 1995, JIS-K7350-2: 1995, JIS-K7350-3: 1996 and JIS-K7350-4: 1996 and methods with reference thereto. Specifically, the evaluation of the change in the color difference of the background at the printing part after irradiation using a fluorescent lamp, the evaluation of the residual ratio of the image concentration by exposure using a xenon weatherometer, the evaluation of the change in the optical reflection concentration by exposure using a xenon weatherometer, the evaluation of the degree of yellowing by using L* a* b* evaluation criteria after exposure using the Suntest CPS light color fading testing machine, the evaluation of the color fading after exposure using a fadeometer, the visual evaluation of the color fading after exposure using a xenon fadeometer, the evaluation of the color concentration retention ratio after exposure of the solar light inside the room, the evaluation of the color concentration retention ratio after exposure using a xenon weatherometer, the evaluation of the C/N after exposure using a fadeometer, the evaluation of the fog concentration after exposure using a fluorescent lamp, the evaluation of the optical reflection concentration after exposure using a fluorescent lamp, the evaluation of the erasability, the color difference ΔE* after exposure using the Atlas fadeometer, the visual evaluation of the color fading after exposure using a carbon arc fadeometer, the evaluation of an organic EL element color conversion characteristic retention ratio, the evaluation of an organic EL display luminance measurement after exposure by a xenon color fading testing machine, and the like are included.

As other evaluation methods, it is possible to evaluate by methods of JIS-K7103, ISO/DIS9050 and methods with reference thereto. Specifically, the appearance evaluation of a polycarbonate coated film after exposure by a UV tester, the evaluation of the blue scale in artificial hair after ultraviolet ray exposure, the evaluation of the water contact angle of a treated cloth for evaluation after exposure using an accelerated weather resistance testing machine, the visual evaluation of a picture which is projected onto the projection screen after exposure using a weather resistance testing machine described in JP2005-55615A, the visual evaluation of the deterioration of the surface of the test body and the change in the design after exposure using a sunshine weatherometer and a metal weatherometer, the visual evaluation of the appearance after light exposure using a metal lamp reflector, the evaluation of the light transmittance of a label for bottle, the evaluation of the deterioration of polypropylene after exposure under the humidity condition using a xenon weatherometer, the evaluation of the deterioration of a hard coat film using a sunshine weatherometer, the evaluation of the deterioration of a base material, the evaluation of the hydrophilic property, the evaluation of the excoriation resistance, the evaluation of the gray scale for the color difference of artificial leather after exposure using a xenon lamp light source, the evaluation of the liquid crystal device characteristics after exposure using a mercury lamp, the evaluation of the adhesion after exposure using a sunshine weatherometer, the evaluation of the degree of a purple patch of turf, the evaluation of the ultraviolet ray transmittance after exposure using a xenon arc light source, the evaluation of the tensile strength, the evaluation of the concrete adhesive speed, the appearance evaluation and the evaluation of the coating film adhesion after exposure using a sunshine weatherometer, the degree of yellowing after exposure using a carbon arc light source, the evaluation of the adhesion, the evaluation of the bond performance using an ultraviolet ray fadeometer, the evaluation of the suppression of the flying of insects when the illumination is lighted on, the evaluation of the degree of yellowing ($\Delta$YI) of a laminated glass using the EYE Super UV tester, the appearance evaluation of the surface after performing a QUV irradiation and a moisture resistant test, the evaluation of the glossiness retention ratio, the evaluation of the color difference over time using the Dew panel optical control weatherometer, the glossiness (DI) in an application state of a wood base material after exposure using a xenon weatherometer, the evaluation of the degree of yellowness index (YI), the evaluation of an ultraviolet ray absorption rate after repetition of the irradiation with ultraviolet ray and the darkness, the evaluation of the color difference $\Delta$E of the color fading of a dye after ultraviolet ray exposure, and the like are included.

EXAMPLE

Description will be given of the present invention in further detail with reference to Examples; however, the present invention is not limited thereto.

Synthesis of Compound (1)

500 mL of toluene was added to 20 g of salicylamide, terephthaloyl chloride was added to the obtained solution at 50° C. dividedly in plural times (the total additive amount: 14.8 g), and the solution after adding was stirred for 2 hours. Next, 2 mL of methanesulfonic acid was added thereto and the solution was refluxed for 4 hours. After the reaction liquid was cooled down to room temperature, a synthetic intermediate A was obtained by filtrating the obtained solid and washing it by water. 100 mL of methanol, 1.2 g of sodium methoxide (28% methanol solution) and 1.0 g of the synthetic intermediate A were added to 1.0 g of benzamidine hydrochloride and the solution was stirred at room temperature for 7 hours. A compound (1) was obtained by filtrating the obtained solid and washing it by water and methanol. Mass measured value $(M+H)^+$: 573.20

Synthesis of Compound (2)

A compound (2) was obtained in the same way except using 14.8 g of isophthaloyl chloride instead of terephthaloyl chloride in the synthesis of the compound (1). Mass measured value $(M+H)^+$: 573.20

Synthesis of Compound (3)

A compound (3) was obtained in the same way except using 14.8 g of phthaloyl chloride instead of terephthaloyl chloride in the synthesis of the compound (1). Mass measured value $(M+H)^+$: 573.20

Synthesis of Compound (4)

A compound (4) was obtained in the same way except using 1.0 g of 2-amidino thiophene instead of benzamidine hydrochloride in the synthesis of the compound (1). Mass measured value $(M+H)^+$: 585.12

Synthesis of Compound (5)

A compound (5) was obtained in the same way except using 15.2 g of thiophene-2,5-dicarboxylic acid dichloride instead of terephthaloyl chloride in the synthesis of the compound (1). Mass measured value $(M+H)^+$: 579.16

Synthesis of Compound (6)

A compound (6) was obtained in the same way except using 0.9 g of 1,3,5-benzene tricarbonyl trichloride instead of terephthaloyl chloride in the synthesis of the compound (1). Mass measured value $(M+H)^+$: 820.28

Synthesis of Compound (7)

A compound (7) was obtained in the same way except using 1.3 g of 2-amidino naphthalene instead of benzamidine hydrochloride in the synthesis of the compound (1). Mass measured value $(M+H)^+$: 673.24

Synthesis of Compound (8)

A compound (8) was obtained in the same way except using 20.3 g of biphenyl-4,4'-dicarboxylic acid dichloride instead of terephthaloyl chloride in the synthesis of the compound (1). Mass measured value $(M+H)^+$: 649.24

Synthesis of Compound (9)

A compound (9) was obtained in the same way except using 18.4 g of 2,6-naphthalene dicarboxylic acid dichloride instead of terephthaloyl chloride in the synthesis of the compound (1). Mass measured value $(M+H)^+$: 623.22

Synthesis of Compound (10)

A compound (10) was obtained in the same way except using 1.4 g of 4-amidino benzoic acid methyl instead of benzamidine hydrochloride in the synthesis of the compound (1). Mass measured value (M+H)$^+$: 689.21

Synthesis of Compound (11)

A compound (11) was obtained in the same way except using 1.2 g of 4-amidino benzonitrile instead of benzamidine hydrochloride in the synthesis of the compound (1). Mass measured value (M+H)$^+$: 623.19

Synthesis of Compound (12)

A compound (12) was obtained in the same way except using 1.2 g of 3-amidino benzonitrile instead of benzamidine hydrochloride in the synthesis of the compound (2). Mass measured value (M+H)$^+$: 623.19

Synthesis of Compound (13)

A compound (13) was obtained in the same way except using 1.7 g of 6-amidino-2-naphthoic acid methyl instead of benzamidine hydrochloride in the synthesis of the compound (1). Mass measured value (M+H)$^+$: 789.25

Synthesis of Compound (14)

A compound (14) was obtained in the same way except using 1.5 g of 6-amidino-2-naphthonitrile instead of benzamidine hydrochloride in the synthesis of the compound (1). Mass measured value (M+H)$^+$: 723.23

Synthesis of Compound (15)

A compound (15) was obtained in the same way except using 1.2 g of 4-amidino benzoyInitrile instead of benzamidine hydrochloride in the synthesis of the compound (5). Mass measured value (M+H)$^+$: 629.15

Synthesis of Compound (16)

A compound (16) was obtained in the same way except using 1.2 g of 4-amidino anisole instead of benzamidine hydrochloride in the synthesis of the compound (1). Mass measured value (M+H)$^+$. 633.23

Synthesis of Compound (17)

A compound (17) was obtained in the same way except using 0.6 g of acetamidine instead of benzamidine hydrochloride in the synthesis of the compound (2). Mass measured value (M+H)$^+$. 449.17

Synthesis of Compound (18)

A compound (18) was obtained in the same way except using 0.9 g of amino(imino)methyl acetate instead of benzamidine hydrochloride in the synthesis of the compound (8). Mass measured value (M+H)$^+$: 613.18

Synthesis of Comparative Compound (1)

A synthesis was performed by a method described in JP2006-225322A, p. 14.

Synthesis of Comparative Compound (2)

A synthesis was performed by a method described in JP1996-53427A (JP-H08-53427A), p. 34.

<Evaluation>

The compounds obtained by the syntheses described above were evaluated for the following items. The results are shown in Table 1.

(Light Resistance)

22% by mass of a PMMA resin (trade name: Dianal BR-80, manufactured by MITSUBISHI RAYON CO., LTD.) was dissolved in methylene chloride to prepare a binder solution. Next, 0.2% by mass of the compound (1) was dissolved in the binder solution to prepare an application liquid. The glass was set to a base material, the application liquid described above was applied thereon by the blade of 200 μm and was dried at 100° C. for 10 minutes, and a film was produced by forming a coating film having a film thickness of 50 μm. In the same way, as to the compounds (2) to (18), the comparative compound (1) and the comparative compound (2), films were produced.

As to the produced films, the absorbance was measured using the spectrophotometer UV-3600 (trade name) manufactured by Shimadzu Corporation. Light was irradiated with respect to the film by a metal halide lamp (trade name: the EYE Super UV tester, manufactured by IWASAKI ELECTRIC CO., LTD.) under conditions of 90 mW/cm$^2$ of illumination, 63° C. of temperature and 50% of humidity, and after irradiation for 600 hours, the residual amounts of each compound were respectively measured. The residual amount was calculated according to the following expression.

$$\text{The residual amount}(\%) = 100 \times (100 - \text{the transmittance after irradiation})/(100 - \text{the transmittance before irradiation})$$

Moreover, the transmittance (measured in a wavelength range from 250 nm to 450 nm) is a value measured at a maximum absorption wavelength of each compound.

As to the residual amount, 90% or more was set to A, 70% or more and less than 90% was set to B, 50% or more and less than 70% was set to C, and less than 50% was set to D.

(Heat Resistance)

A pellet of a polyethylene terephthalate resin having the intrinsic viscosity of 0.78 (dl/g) was dried at 170° C. for 6 hours was mixed with the compound described above to put into an extruder. The pellet was melted and kneaded at 280° C. of the melting temperature to obtain an ultraviolet absorber-containing pellet. The ultraviolet absorber-containing pellet was mixed with a polyethylene terephthalate resin so that the amount of compound becomes 0.5 g/m$^2$ and was melted and kneaded at 280° C., and a film having a thickness of 100 μm was obtained. When producing a film, the dirt of a film forming device due to adhesion of the compound which was volatilized was observed.

The case where the adhesion was not recognized at all was set to A, the case where the adhesion was slightly recognized was set to B, and the case where the adhesion noticeably was recognized was set to C.

(Ultraviolet Ray Shielding Effect)

In the evaluation of heat resistance described above, the produced film was arranged on a poster as a protective film and an outdoor exposure test was conducted for 5,000 hours. The color fading of a picture on a poster was visually evaluated.

The case where the color fading was not recognised at all was set to A, the case where the color was slightly faded was set to B, the case where the color was largely faded was set to C, and the case where the color was completely faded was set to D.

TABLE 1

| | Compound | Light resistance | Heat resistance | Ultraviolet ray shielding effect |
|---|---|---|---|---|
| Example 1 | Compound (1) | B | A | B |
| Example 2 | Compound (2) | B | A | C |
| Example 3 | Compound (3) | B | A | C |
| Example 4 | Compound (4) | C | A | A |
| Example 5 | Compound (5) | C | A | A |
| Example 6 | Compound (6) | B | A | C |
| Example 7 | Compound (7) | C | A | A |
| Example 8 | Compound (8) | C | A | A |
| Example 9 | Compound (9) | C | A | A |
| Example 10 | Compound (10) | A | A | B |
| Example 11 | Compound (11) | A | A | B |
| Example 12 | Compound (12) | A | A | C |
| Example 13 | Compound (13) | C | A | A |
| Example 14 | Compound (14) | B | A | A |
| Example 15 | Compound (15) | B | A | A |
| Example 16 | Compound (16) | C | A | B |
| Example 17 | Compound (17) | C | A | C |
| Example 18 | Compound (18) | C | A | B |
| Comparative Example 1 | Comparative Compound (1) | D | C | D |
| Comparative Example 2 | Comparative Compound (2) | D | B | D |

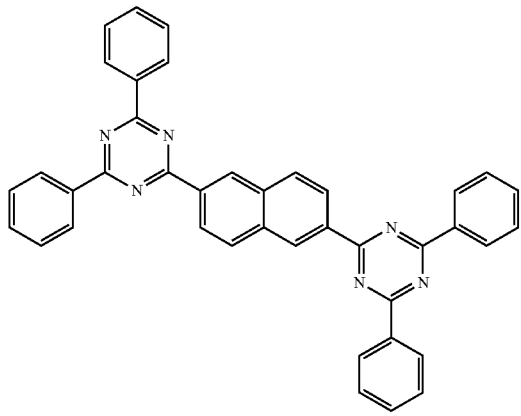 [SMILES: c1ccc(-c2nc(-c3ccccc3)nc(-c3ccc4cc(-c5nc(-c6ccccc6)nc(-c6ccccc6)n5)ccc4c3)n2)cc1]

Comparative compound (1)

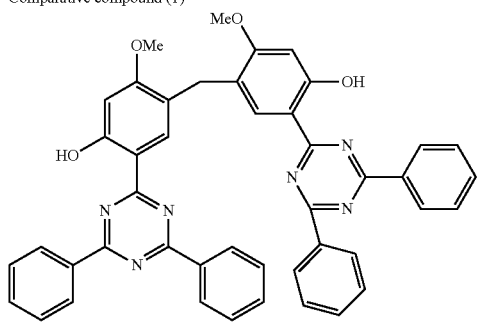

Comparative compound (2)

As it is clear from the results in Table 1, it was found that the compound in the present invention had high performance as an ultraviolet absorber, compared with the comparative compound (1) which did not have a hydroxyl group in a structure. Furthermore, it was found that the compound of the present invention has excellent light resistance and ultraviolet ray shielding effect, also in a case of comparing with the comparative compound (2) having a structure in which the conjugation in a part of a linking group was blocked.

In addition, it was found that the compound in which $X^1$ in the general formula (1) of the present invention was a benzene ring and the compound in which $X^1$ had an electron-withdrawing group as a substituent were excellent in light resistance and the compound having a naphthalene structure in a structure in the general formula (1) of the present invention was excellent in an ultraviolet ray shielding effect, in the comparison between the compounds of the present invention.

The present application is a continuation application of International Application No PCT/JP2012/074347, filed Sep. 24, 2012, which claims priority to Japanese Patent Application No. 2011-215631, filed Sep. 29, 2011. The contents of these applications are incorporated herein by reference in their entirety.

What is claimed is:

1. A compound represented by the following general formula (1),

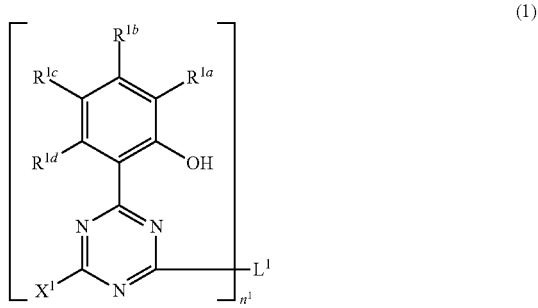

(1)

in the general formula (1), $L^1$ represents a divalent to decavalent aromatic ring residue or a divalent to decavalent heterocycle residue, $n^1$ represents an integer of 2 to 10, $X^1$ represents a hydrogen atom or a substituent, $R^{1a}$, $R^{1b}$, $R^{1c}$ and $R^{1d}$ each independently represent a hydrogen atom or a substituent and may be bonded to each other to form a ring.

2. The compound according to claim 1, wherein $X^1$ in the general formula (1) represents an aromatic ring residue or a heterocycle residue.

3. The compound according to claim 1, wherein the compound represented by the general formula (1) is a compound represented by the following general formula (2),

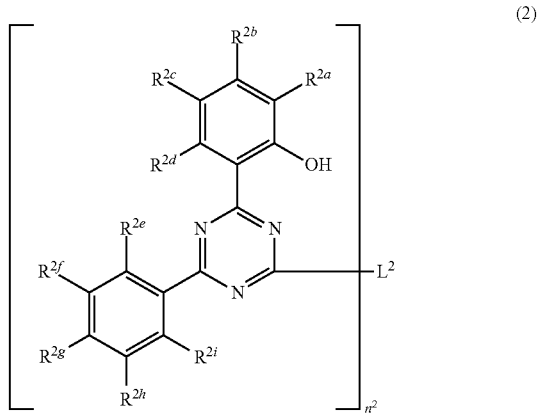

(2)

in the general formula (2), $L^2$ represents a divalent to decavalent aromatic ring residue or a divalent to decavalent heterocycle residue, $n^2$ represents an integer of 2 to 10, $R^{2a}$, $R^{2b}$, $R^{2c}$ and $R^{2d}$ each independently represent a hydrogen atom or a substituent and may be bonded to each other to form a ring, $R^{2e}$, $R^{2f}$, $R^{2g}$, $R^{2h}$ and $R^{2i}$ each independently represent a hydrogen atom or a substituent and may be bonded to each other to form a ring.

4. The compound according to claim 3,
wherein any of $R^{2e}$, $R^{2f}$, $R^{2g}$, $R^{2h}$ and $R^{2i}$ in the general formula (2) represents an electron-withdrawing group, or in a case where $R^{2e}$, $R^{2f}$, $R^{2g}$, $R^{2h}$ and $R^{2i}$ are bonded to each other to form a ring, the ring has an electron-withdrawing group as a substituent.

5. The compound according to claim 4,
wherein the electron-withdrawing group is represented by —CN or —COOR$^r$,
R$^r$ represents a hydrogen atom or a substituent.

6. The compound according to claim 1,
wherein $L^1$ in the general formula (1) is a group represented by a divalent aromatic ring residue or heterocycle residue.

7. The compound according to claim 3,
wherein $L^2$ in the general formula (2) is a group represented by a divalent aromatic ring residue or heterocycle residue.

8. The compound according to claim 1,
wherein $L^1$ in the general formula (1) is a divalent aromatic ring residue and the aromatic ring residue is a benzene ring or a naphthalene ring.

9. The compound according to claim 3,
wherein $L^2$ in the general formula (2) is a divalent aromatic ring residue and the aromatic ring residue is a benzene ring or a naphthalene ring.

10. The compound according to claim 5,
wherein $L^2$ in the general formula (2) is a divalent aromatic ring residue and the aromatic ring residue is a benzene ring or a naphthalene ring.

11. The compound according to claim 3,
wherein the compound represented by the general formula (2) is a compound represented by the following general formula (3),

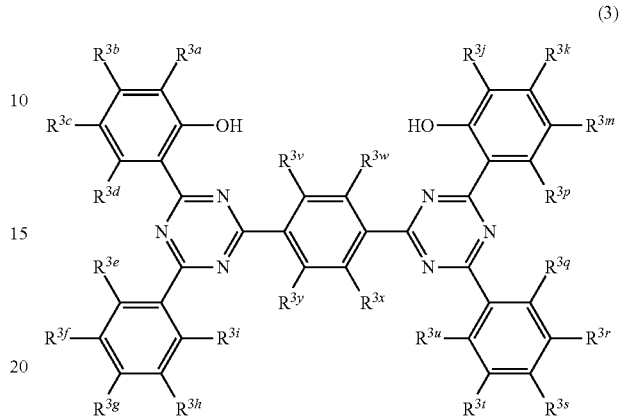

(3)

in the general formula (3), $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3m}$, $R^{3p}$, $R^{3q}$, $R^{3r}$, $R^{3s}$, $R^{3t}$, $R^{3u}$, $R^{3v}$, $R^{3w}$, $R^{3x}$ and $R^{3y}$ each independently represent a hydrogen atom or a substituent and may be bonded to each other to form a ring.

12. An ultraviolet absorber containing:
the compound according to claim 1.

13. A resin composition containing at least:
the compound according to claim 1; and
a resin.

* * * * *